US012648177B2

(12) United States Patent
Lee et al.

(10) Patent No.:     US 12,648,177 B2
(45) Date of Patent:          Jun. 2, 2026

(54) THIN-FILM TRANSISTORS FOR DETECTING MINIATURE TARGETS

(71) Applicant: Taiwan Semiconductor Manufacturing Company, Ltd., Hsin-Chu (TW)

(72) Inventors: Wei Lee, Hsinchu City (TW); Chung-Liang Cheng, Changhua County (TW); Pei-Wen Liu, Hsinchu City (TW); Ke-Wei Su, Hsinchu County (TW); Kuan-Lun Cheng, Hsin-Chu (TW)

(73) Assignee: TAIWAN SEMICONDUCTOR MANUFACTURING COMPANY, LTD., Hsinchu (TW)

( * ) Notice:    Subject to any disclaimer, the term of this patent is extended or adjusted under 35 U.S.C. 154(b) by 730 days.

(21) Appl. No.: 17/876,920

(22) Filed:     Jul. 29, 2022

(65)              Prior Publication Data

US 2024/0038894 A1      Feb. 1, 2024

(51) Int. Cl.
     H10D 30/67      (2025.01)
     G01N 33/543     (2006.01)
     H10D 87/00      (2026.01)
     H10D 99/00      (2025.01)

(52) U.S. Cl.
     CPC ..... H10D 30/6728 (2025.01); G01N 33/5438 (2013.01); H10D 30/6755 (2025.01); H10D 87/00 (2025.01); H10D 99/00 (2025.01)

(58) Field of Classification Search
     CPC ........... H10D 30/6728; H10D 30/6755; H10D 87/00; H10D 99/00; H10D 84/08; H10D 84/83; H10D 88/00; G01N 33/5438

USPC .......................................................... 257/43
See application file for complete search history.

(56)                References Cited

U.S. PATENT DOCUMENTS

| | | | |
|---|---|---|---|
| 8,601,416 B2 | 12/2013 | Kuo et al. | |
| 8,605,523 B2 | 12/2013 | Tao et al. | |
| 8,630,132 B2 | 1/2014 | Cheng et al. | |
| 8,760,948 B2 | 6/2014 | Tao et al. | |
| 8,762,900 B2 | 6/2014 | Shin et al. | |
| 8,775,993 B2 | 7/2014 | Huang et al. | |
| 8,887,116 B2 | 11/2014 | Ho et al. | |
| 10,446,689 B1 * | 10/2019 | Huang ............... | H10D 30/6734 |
| 2014/0032871 A1 | 1/2014 | Hsu et al. | |
| 2014/0101623 A1 | 4/2014 | Chen et al. | |
| 2014/0153321 A1 | 6/2014 | Liaw | |
| 2014/0153345 A1 | 6/2014 | Kim et al. | |
| 2014/0177352 A1 | 6/2014 | Lum | |

(Continued)

FOREIGN PATENT DOCUMENTS

TW          201913883 A      4/2019

*Primary Examiner* — Duy T Nguyen
*Assistant Examiner* — Jiyoung Oh
(74) *Attorney, Agent, or Firm* — HAYNES AND BOONE, LLP

(57)                ABSTRACT

An interconnect structure is disposed over a semiconductor substrate. The interconnect structure includes a plurality of interconnect layers. A first thin-film transistor (TFT) and a second TFT are disposed over the semiconductor substrate. The first TFT and the second TFT each vertically extend through at least a subset of the interconnect layers. An opening is formed in the interconnect structure. The opening is disposed between the first TFT and the second TFT. A sensing film is disposed over a bottom surface and side surfaces of the opening.

20 Claims, 24 Drawing Sheets

(56) References Cited

U.S. PATENT DOCUMENTS

| | | | |
|---|---|---|---|
| 2014/0201692 A1 | 7/2014 | Chen et al. | |
| 2014/0233330 A1 | 8/2014 | Ko et al. | |
| 2014/0237435 A1 | 8/2014 | Chen et al. | |
| 2014/0241077 A1 | 8/2014 | Katoch et al. | |
| 2014/0269114 A1 | 9/2014 | Yang et al. | |
| 2014/0282337 A1 | 9/2014 | Yuh et al. | |
| 2014/0304670 A1 | 10/2014 | Su et al. | |
| 2014/0310675 A1 | 10/2014 | Liu et al. | |
| 2014/0325464 A1 | 10/2014 | Hsu et al. | |
| 2015/0330941 A1* | 11/2015 | Smith | G01N 27/4148 |
| | | | 257/253 |
| 2017/0102358 A1* | 4/2017 | Hoffman | H10D 64/254 |
| 2017/0227485 A1* | 8/2017 | Cai | H10D 10/60 |
| 2020/0098932 A1* | 3/2020 | Lajoie | H10D 30/6746 |
| 2021/0278396 A1* | 9/2021 | Goldsmith | G01N 33/5438 |

* cited by examiner

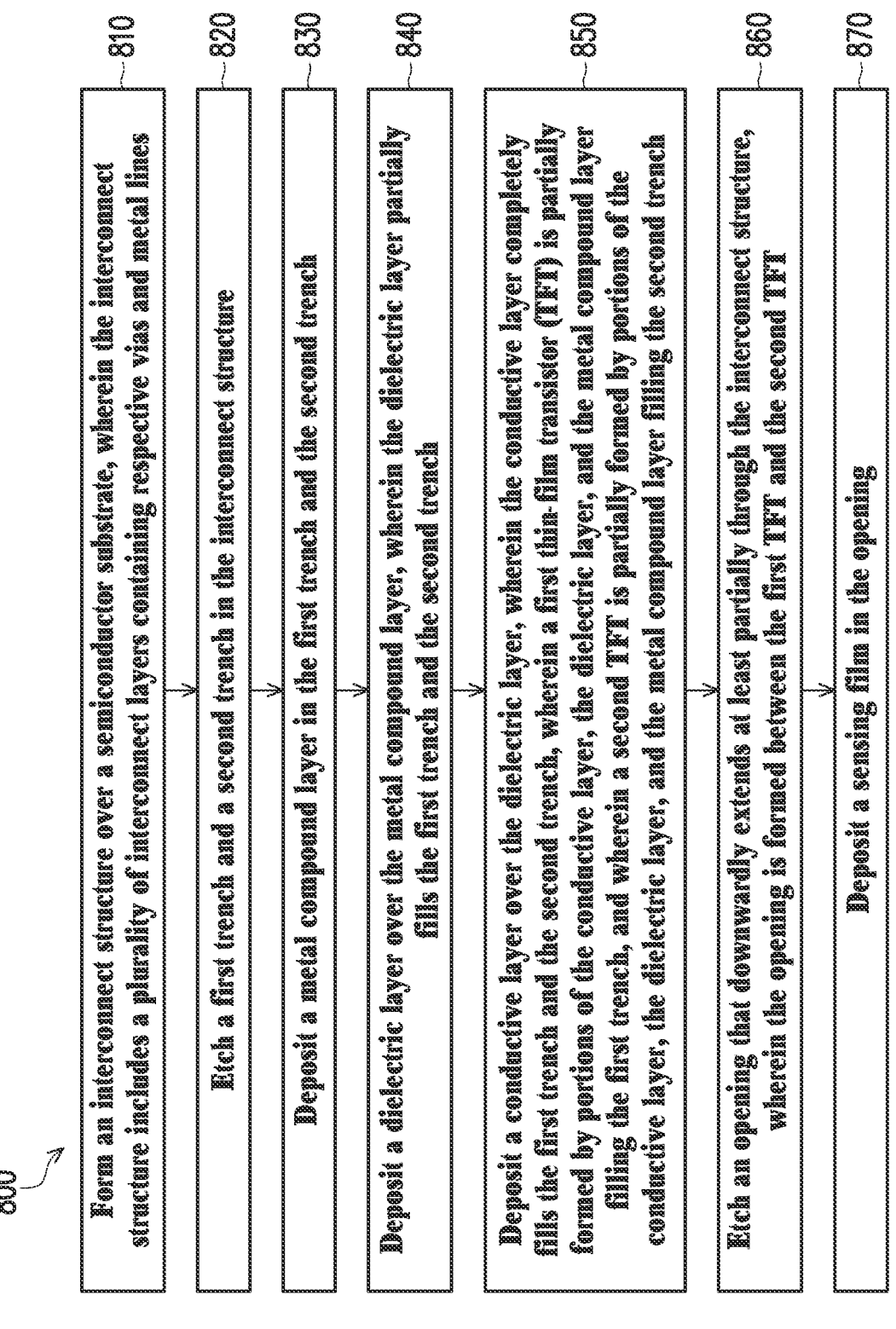

800

810 — Form an interconnect structure over a semiconductor substrate, wherein the interconnect structure includes a plurality of interconnect layers containing respective vias and metal lines 820 — Etch a first trench and a second trench in the interconnect structure 830 — Deposit a metal compound layer in the first trench and the second trench 840 — Deposit a dielectric layer over the metal compound layer, wherein the dielectric layer partially fills the first trench and the second trench 850 — Deposit a conductive layer over the dielectric layer, wherein the conductive layer completely fills the first trench and the second trench, wherein a first thin-film transistor (TFT) is partially formed by portions of the conductive layer, the dielectric layer, and the metal compound layer filling the first trench, and wherein a second TFT is partially formed by portions of the conductive layer, the dielectric layer, and the metal compound layer filling the second trench 860 — Etch an opening that downwardly extends at least partially through the interconnect structure, wherein the opening is formed between the first TFT and the second TFT 870 — Deposit a sensing film in the opening

FIG. 23

THIN-FILM TRANSISTORS FOR DETECTING MINIATURE TARGETS

BACKGROUND

The semiconductor integrated circuit (IC) industry has experienced exponential growth. Technological advances in IC materials and design have produced generations of ICs where each generation has smaller and more complex circuits than the previous generation. In the course of IC evolution, functional density (i.e., the number of interconnected devices per chip area) has generally increased while geometry size (i.e., the smallest component (or line) that can be created using a fabrication process) has decreased. This scaling down process generally provides benefits by increasing production efficiency and lowering associated costs.

As semiconductor devices shrink in size but increase in sophistication, they can be deployed in a great variety of applications. These applications may include life-science applications, which may pertain to medical diagnostics or environmental monitoring applications. For example, semiconductor circuitry may be implemented in devices to test the presence of certain types of miniature targets, which may include ions, nucleic acids, polarized molecules, antigens, antibodies, enzymes, cells, proteins, viruses, or bacteria. However, conventional methods and/or structures of implementing semiconductor circuitry in these test devices may be expensive and have sub-optimal efficiency, and therefore have not been entirely satisfactory.

BRIEF DESCRIPTION OF THE DRAWINGS

The present disclosure is best understood from the following detailed description when read with the accompanying figures. It is emphasized that, in accordance with the standard practice in the industry, various features are not drawn to scale and are used for illustration purposes only. In fact, the dimensions of the various features may be arbitrarily increased or reduced for clarity of discussion.

FIG. 23 illustrates a flowchart of a method according to various aspects of the present disclosure.

DETAILED DESCRIPTION

Figure 1:
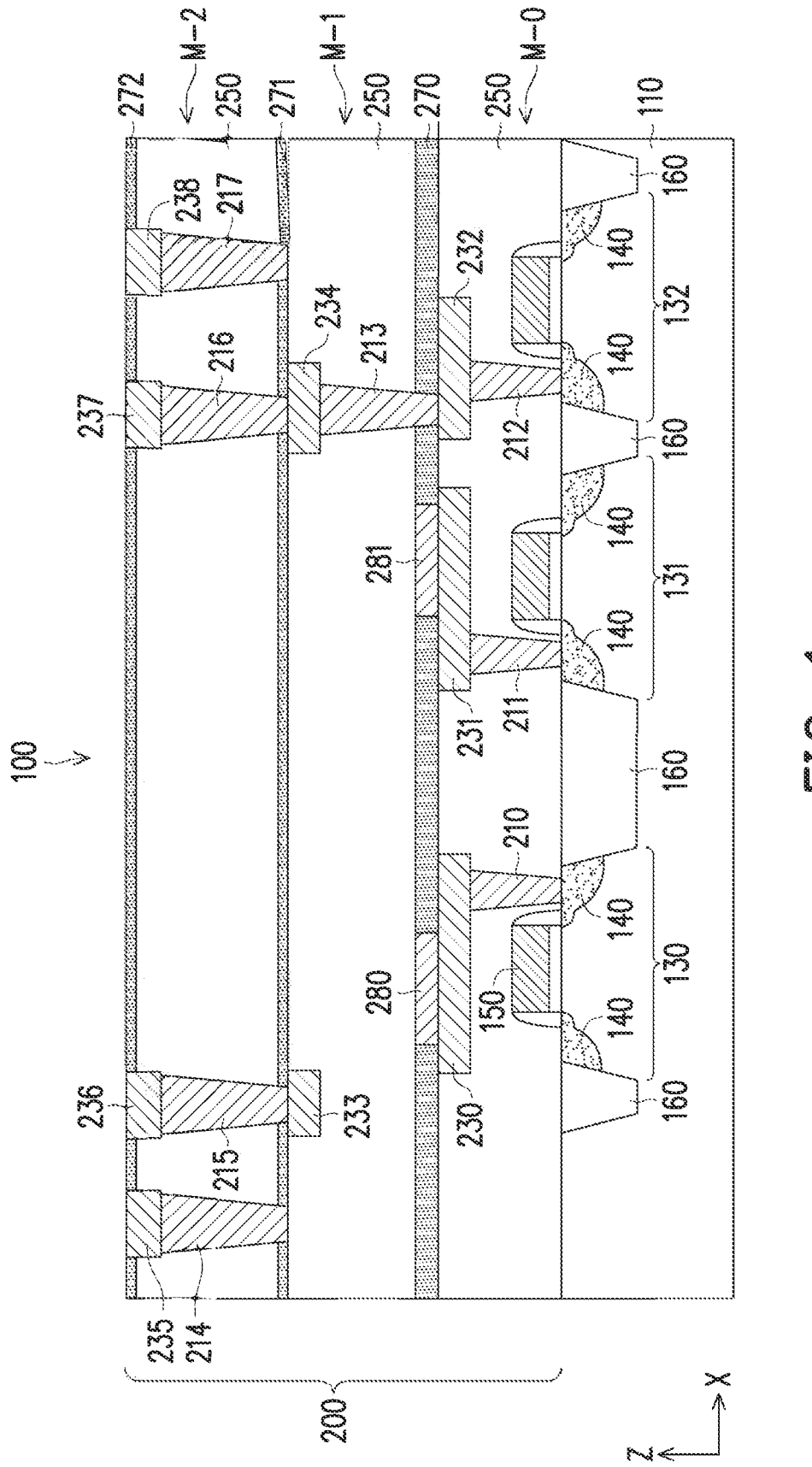
FIGS. 1-14 are cross-sectional side views of a semiconductor device at various stages of fabrication according to various aspects of the present disclosure.

The following disclosure provides many different embodiments, or examples, for implementing different features of the disclosure. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

In addition, the present disclosure may repeat reference numerals and/or letters in the various examples. This repetition is for the purpose of simplicity and clarity and does not in itself dictate a relationship between the various embodiments and/or configurations discussed. Moreover, the formation of a feature on, connected to, and/or coupled to another feature in the present disclosure that follows may include embodiments in which the features are formed in direct contact, and may also include embodiments in which additional features may be formed interposing the features, such that the features may not be in direct contact. In addition, spatially relative terms, for example, "lower," "upper," "horizontal," "vertical," "above," "over," "below," "beneath," "up," "down," "top," "bottom," etc., as well as derivatives thereof (e.g., "horizontally," "downwardly," "upwardly," etc.) are used for ease of the present disclosure of one features relationship to another feature. The spatially relative terms are intended to cover different orientations of the device including the features. Still further, when a number or a range of numbers is described with "about," "approximate," and the like, the term is intended to encompass numbers that are within a reasonable range including the number described, such as within +/-10% of the number described or other values as understood by person skilled in the art. For example, the term "about 5 nm" encompasses the dimension range from 4.5 nm to 5.5 nm.

The present disclosure is generally related to semiconductor devices, and more particularly to semiconductor devices that are implemented in diagnostic devices to sense or detect the presence of certain types of miniature targets, including but not limited to ions, nucleic acids, polarized molecules, antigens, antibodies, enzymes, cells, proteins, viruses, bacteria, or other biological particles that are smaller than a few hundred microns. For example, a nasal swab may contain semiconductor circuitry configured to detect the presence of the COVID-19 virus. When a user swabs his/her nasal cavity with such a nasal swab device, the swabbed particles or substance may be collected, for example, in the form of nasal fluid. The swabbed nasal fluid may be delivered to semiconductor circuitry for detection of the miniature targets. In some embodiments, the semiconductor circuitry may be embedded in the nasal swab device. In other embodiments, the semiconductor circuitry may be implemented in an analyzer device that is separate from the nasal swab device. Regardless, the particles or substance containing the COVID-19 virus, when forced into a sensing region of the semiconductor circuitry, may cause the semiconductor circuitry to generate certain types of electrical signals (e.g., a predefined level of electrical voltage or current), which may be an indication that the user does indeed have COVID-19. Other types of miniature targets (which may be associated with other illnesses or diseases or certain types of environmental situations) may be detected in a similar manner.

However, the diagnostic devices using conventional semiconductor circuitry may have certain drawbacks. One such drawback is the high cost of fabrication, since the conventional semiconductor circuitry in these diagnostic devices is formed on a silicon-on-insulator (SOI) structure, which may be expensive. Another drawback is the sub-optimal efficiency, since the conventional semiconductor circuitry in these diagnostic devices may not be able to fully capture the miniature targets in the designated miniature-target sensing regions. Consequently, the accuracy of the diagnostic devices may be degraded.

The present disclosure provides a novel semiconductor device (and a unique fabrication flow thereof) in which thin-film-transistors (TFTs) are formed on a bulk semiconductor wafer (e.g., a silicon wafer), which is cheaper than the conventional SOI structures. In addition, the unique TFT structures of the present disclosure allow the miniature targets to be captured and/or detected more efficiently, which improves the signal-to-noise ratio and the accuracy of the diagnostic devices, as will be discussed below in more detail.

FIGS. 1-13 illustrate a series of cross-sectional side views of a semiconductor device 100 at various stages of fabrication according to embodiments of the present disclosure. FIGS. 1-13 correspond to a cross-section taken along a plane defined by a X-direction as its horizontal direction and a Z-direction as its vertical direction. FIGS. 1-13 may also be referred to as X-cut views.

The semiconductor device 100 includes a substrate 110, which may be a part of a bulk semiconductor wafer. In some embodiments, the substrate 110 may comprise an elementary (single element) semiconductor, such as silicon, germanium, and/or other suitable materials; a compound semiconductor, such as silicon carbide, gallium arsenic, gallium phosphide, indium phosphide, indium arsenide, indium antimonide, and/or other suitable materials; an alloy semiconductor such as SiGe, GaAsP, AlInAs, AlGaAs, GaInAs, GaInP, GaInAsP, and/or other suitable materials. The substrate 110 may be a single-layer material having a uniform composition. Alternatively, the substrate 110 may include multiple material layers having similar or different compositions suitable for IC device manufacturing.

A plurality of transistors, such as transistors 130, 131, and 132, may be formed in and over the substrate 110. The transistors 130-132 may each include doped regions, such as source/drain regions 140, that are formed in the substrate 110. The source/drain regions 140 may be doped with n-type dopants, such as phosphorus or arsenic, and/or p-type dopants, such as boron, depending on design requirements. The source/drain regions 140 may be formed in a p-well structure, in an n-well structure, in a dual-well structure, or using a raised structure. The source/drain regions 140 may be formed by implantation of dopant atoms, in-situ doped epitaxial growth, and/or other suitable techniques.

The transistors 130-132 may also each include a gate structure 150 that is formed over the substrate 110. The gate structure 150 may include a high-k metal gate (HKMG) structures that contain a high-k gate dielectric and a metal gate electrode. The HKMG structure may be formed by a gate replacement process. In the gate replacement process, a dummy gate structure (e.g., containing a dummy silicon oxide gate dielectric and a polysilicon gate electrode) is formed first, and then the source/drain regions 140 are formed in the substrate 110. The location of the dummy gate structure defines the locations of the source/drain regions 140. As such, the source/drain regions 140 are formed in regions of the substrate 110 on opposite sides of the dummy gate structure.

The dummy gate structure is then removed and replaced by the HKMG structure. In some embodiments, the HKMG structure may include a high-k gate dielectric and a metal gate electrode formed over the high-k gate dielectric. Example materials of the high-gate k dielectric include hafnium oxide, zirconium oxide, aluminum oxide, hafnium dioxide-alumina alloy, hafnium silicon oxide, hafnium silicon oxynitride, hafnium tantalum oxide, hafnium titanium oxide, hafnium zirconium oxide, or combinations thereof. The metal gate electrode may include one or more work function metal layers and one or more fill metal layers. The work function metal layers may be configured to tune a work function of the respective transistor. Example materials for the work function metal layers may include titanium nitride (TiN), Titanium aluminide (TiAl), tantalum nitride (TaN), titanium carbide (Tic), tantalum carbide (TaC), tungsten carbide (WC), titanium aluminum nitride (TiAlN), zirconium aluminide (ZrAl), tungsten aluminide (WAl), tantalum aluminide (TaAl), hafnium aluminide (HfAl), or combinations thereof. The fill metal layer may serve as a main conductive portion of the gate electrode layer.

The HKMG structure may also include gate spacers formed on sidewalls of the high-k gate dielectric layer and the metal gate electrode layer. The gate spacers may be formed as a part of the dummy gate structures, but they are not removed when the dummy gate dielectric and dummy gate electrode are removed. Though not depicted herein, the gate structure 150 may include additional material layers, such as an interfacial layer between the gate dielectric layer and the substrate 110, a capping layer, other suitable layers, or combinations thereof.

The transistors 130-132 are physically and electrically separated from one another by a plurality of isolation structures 160. The isolation structures 160 may include silicon oxide, silicon nitride, silicon oxynitride, fluoride-doped silicate glass (FSG), a low-k dielectric material, and/or other suitable materials. In some embodiments, the isolation structures 160 may include shallow trench isolation (STI) features. In one embodiment, the isolation structures 160 are formed by etching trenches in the substrate 110, and subsequently filling the trenches with an isolating material described above, followed by a chemical mechanical planarization (CMP) process. Other isolation structure such as field oxide, local oxidation of silicon (LOCOS), and/or other suitable structures may also be implemented as the isolation structures 160. Alternatively, the isolation structures 160 may include a multi-layer structure, for example, having one or more thermal oxide liner layers.

A multi-layer interconnect structure 200 is formed over the substrate 110. The multi-layer interconnect structure 200 includes a plurality of interconnect layers, which is also interchangeably referred to herein as metal layers, such as a Metal-0 (M-0) layer, a Metal-1 (M-1) layer, . . . , a Metal-N (M-N) layer. The metal layers each include a plurality of conductive interconnecting elements such as metal lines and conductive vias or contacts. The metal lines in each metal layer extend horizontally, and the metal lines from different metal layers are vertically interconnected together by the conductive vias or contacts. Conductive materials such as copper, cobalt, aluminum, tungsten, ruthenium, or combinations thereof, may be used to implement the metal lines and/or the vias/contacts. Electrical access to the various components of the semiconductor devices 100 is made possible through the metal lines and the vias.

For the sake of providing a simple illustration, the Metal-0 layer, Metal-1 layer, and the Metal-2 layer of the interconnect structure 200 are illustrated herein. For example, vias 210-212 and metal lines 230-232 are implemented in the M-0 layer. The vias 210-212 are each electrically connected to one of the source/drain regions 140 of the transistors 130-132, respectively. The metal lines 230-232 are electrically connected to the vias 210-212, respectively. Via 213 and metal lines 233-234 are implemented in the M-1 layer, where the via 213 is electrically connected to the metal line 232. Vias 214-217 and metal lines 235-238 are implemented in the M-2 layer. The vias 215 and 216 are electrically connected to the metal lines 233-234, respectively. The metal lines 235-238 are electrically connected to the vias 214-217, respectively.

The interconnect structure 200 also includes an electrically insulating material, such as an interlayer dielectric (ILD) material 250 that is implemented in each of the interconnect layers. The vias/contacts 210-217 and the metal lines 230-238 are embedded in, or surrounded by the ILD 250 in each of the interconnect layers. In some embodiments, the ILD 250 may include silicon oxide, silicon nitride, or a low-k dielectric material.

The interconnect structure further includes a plurality of etching-stop layers (ESL) 270, 271, and 272. The ESL 270 is formed over the M-0 layer before the M-1 layer is formed, the ESL 271 is formed over the M-1 layer before the M-2 layer is formed, and the ESL 272 is formed over the M-2 layer. The ESLs 270-272 may contain materials (e.g., dielectric materials) that have etching selectivities with the ILD 250 and with the vias 210-217 and the metal lines 230-238. In some embodiments, the ESL 270-272 may have different material compositions from one another.

Note that conductive pads 280-281 are formed in the ESL 270 before the M-1 and M-2 layers are formed. For example, portions of the ESL 270 may be etched open to partially expose the upper surfaces of the metal lines 230 and 231, and these openings are then filled with a conductive material to form the conductive pads 280-281. The conductive material may include TiN in some embodiments. In other embodiments, the conductive material may include Ti, Ta, W, Mo, Si, O, N, Ni, Co, Ru, Au, Ag, Pt, Mn, Cu, or combinations thereof. The conductive pads 280 and 281 allow for electrical access to the transistors 130 and 131, respectively. In some embodiments, the conductive pads 280-281 may each serve as a portion of a channel region of a respective thin-film transistor (TFT), which is to be formed through the fabrication processes discussed below.

Figure 2:
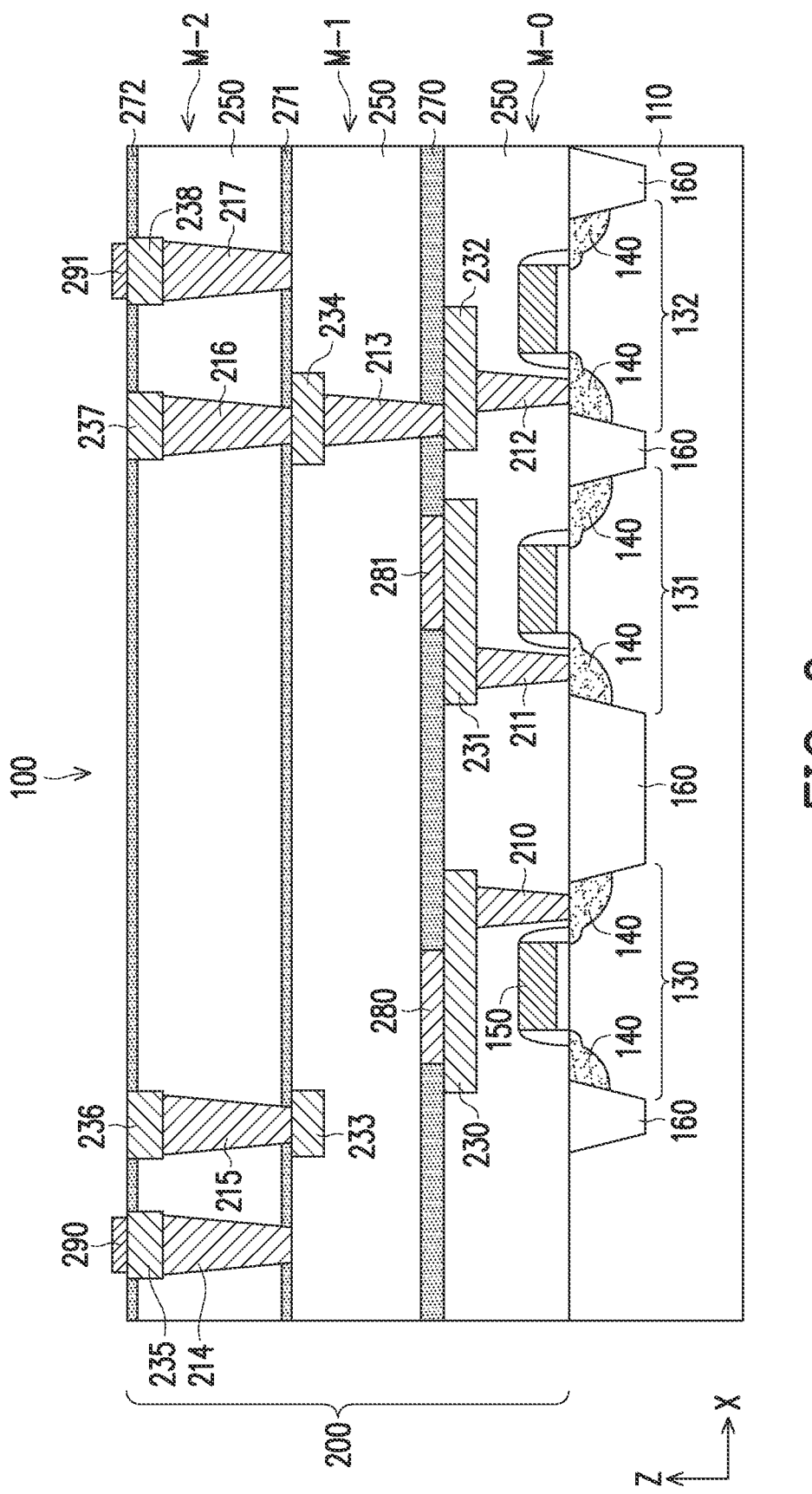

Referring now to FIG. 2, the ESL 272 may be etched back until the upper surfaces of the metal lines 235-238 are exposed. Conductive pads 290 and 291 are then formed over the metal lines 235 and 238, respectively. The conductive pads 290 and 291 may be formed by depositing a conductive material over the upper surfaces of the ILD 250 and the metal lines 235-238 using a deposition process such as chemical vapor deposition (CVD), physical vapor deposition (PVD), or atomic layer deposition (ALD), and then patterning the deposited conductive material into the conductive pads 290 and 291. In some embodiments, the conductive pads 290-291 include TiN. In other embodiments, the conductive pads 290-291 may include Ti, Ta, W, Mo, Si, O, N, Ni, Co, Ru, Au, Ag, Pt, Mn, Cu, or combinations thereof.

Figure 3:
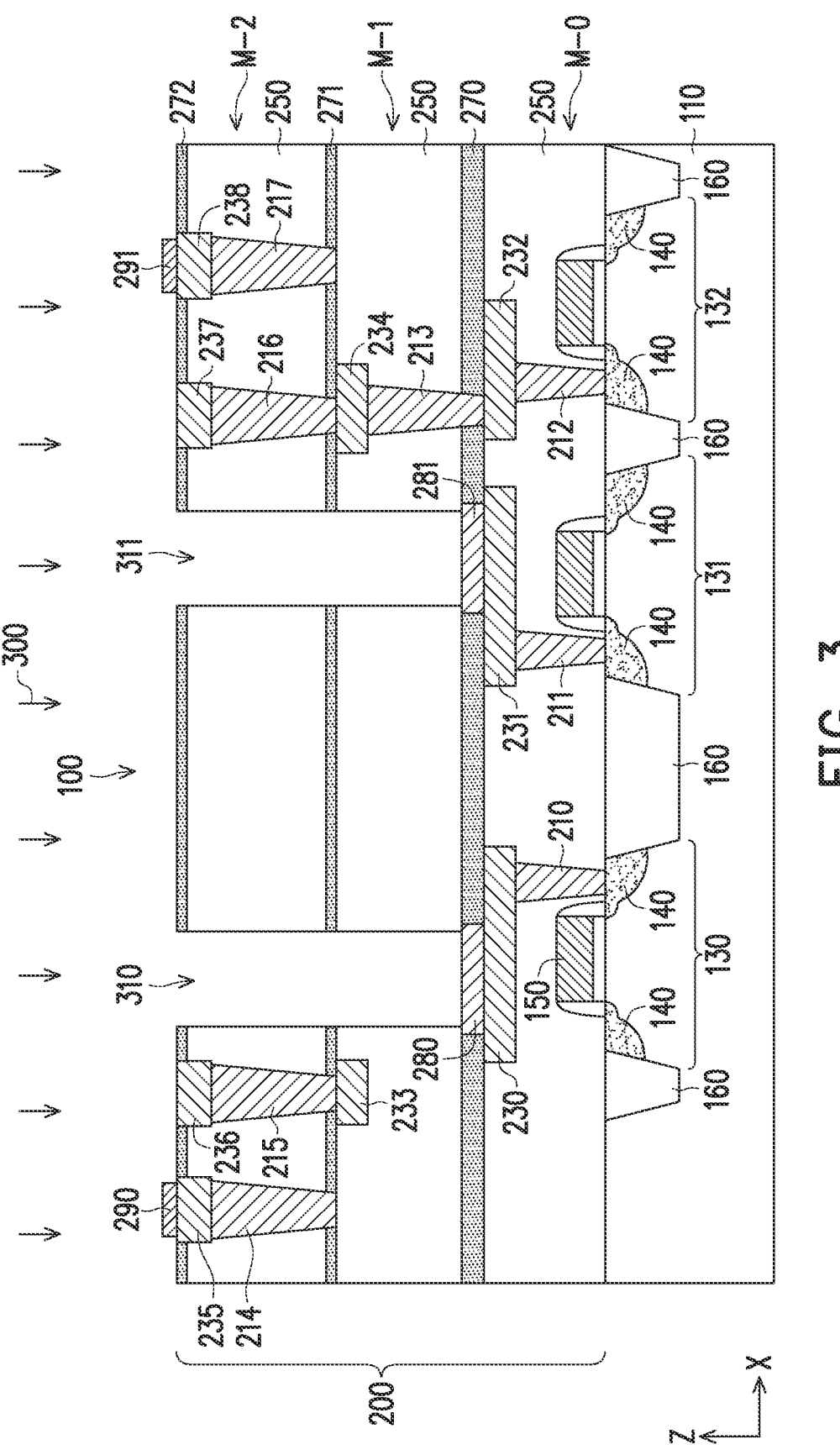

Referring now to FIG. 3, a gate trench etching process 300 is performed to the semiconductor device 100 to form trenches 310 and 311. In some embodiments, the gate trench etching process 300 may include a dry etching process in some embodiments or a wet etching process in other embodiments. The trenches 310-311 extend vertically downwardly through the M-2 and M-1 layers and expose the upper surfaces of the conductive pads 280-281, respectively. It is understood that gate structures and channel regions of the TFTs will be formed in these trenches 310-311 in subsequent processes.

Figure 4:
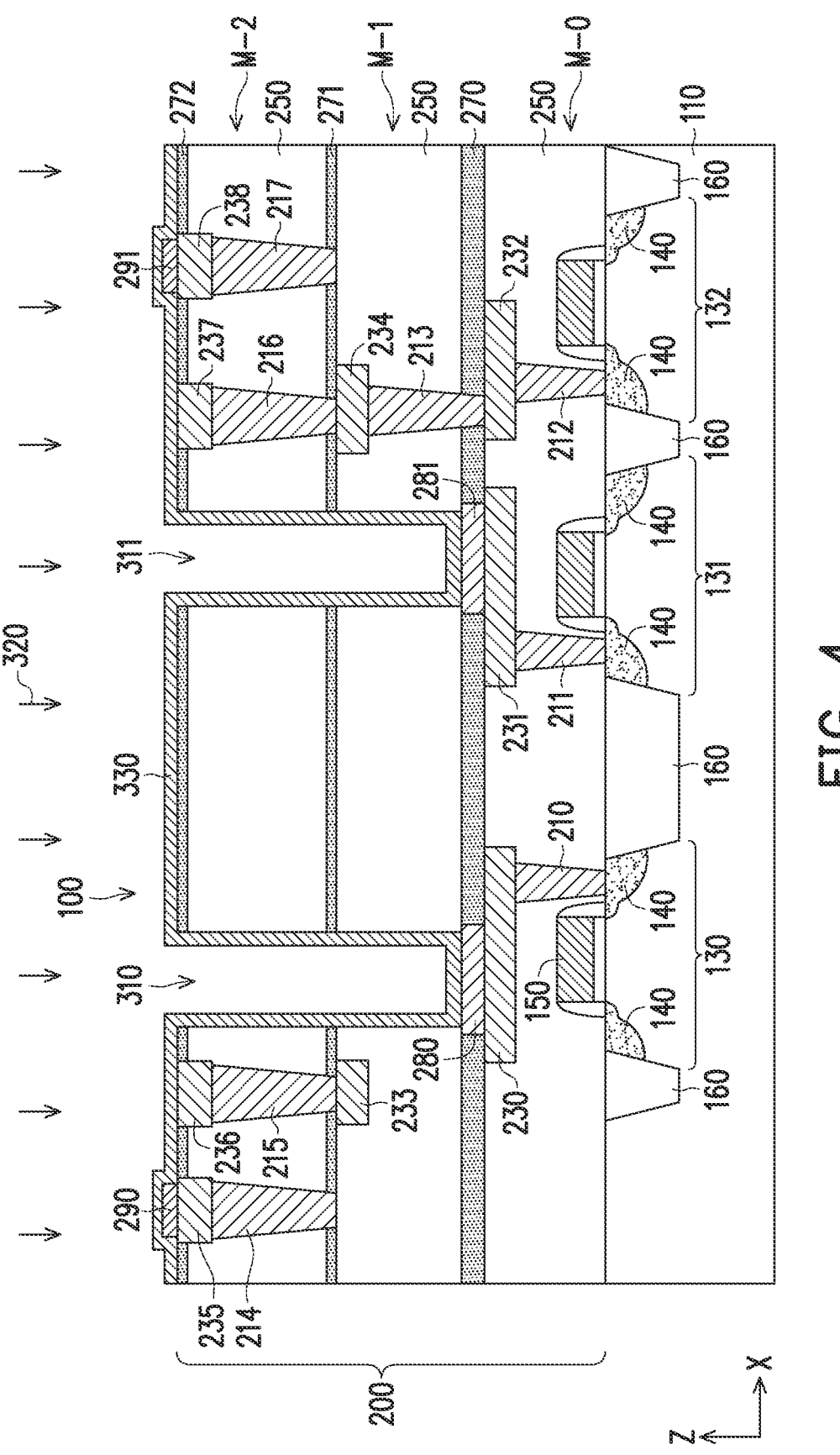

Referring now to FIG. 4, a deposition process 320 is performed to deposit a metal compound layer 330 over the exposed upper surfaces of the semiconductor device 100. For example, the metal compound layer 330 is formed to partially fill in the trenches 310-311, including on the side surfaces and the bottom surfaces of the trenches 310-311 (which correspond to the side surfaces of the ILD 250 and the exposed upper surfaces of the conductive pads 280-281). Portions of the metal compound layer 330 are also formed on the upper surfaces of the ESL 272, the metal lines 235-238, and the conductive pads 290-291. In some embodiments, the deposition process 320 may include an ALD process to accurately control the thickness of the metal compound layer 330. In other embodiments, the deposition process 320 may include a CVD process or a PVD process. The metal compound layer 330 may be formed to have a metal compound material composition, for example Indium-Gallium-Zinc-Oxide (IGZO) in some embodiments. In other embodiments, the metal compound layer 330 may include In, Ga, Zn, O, Al, Sn, Ni, or combinations thereof. It is understood that portions of the metal compound layer 330 will serve as the conductive channel of the to-be-formed TFTs.

Figure 5:
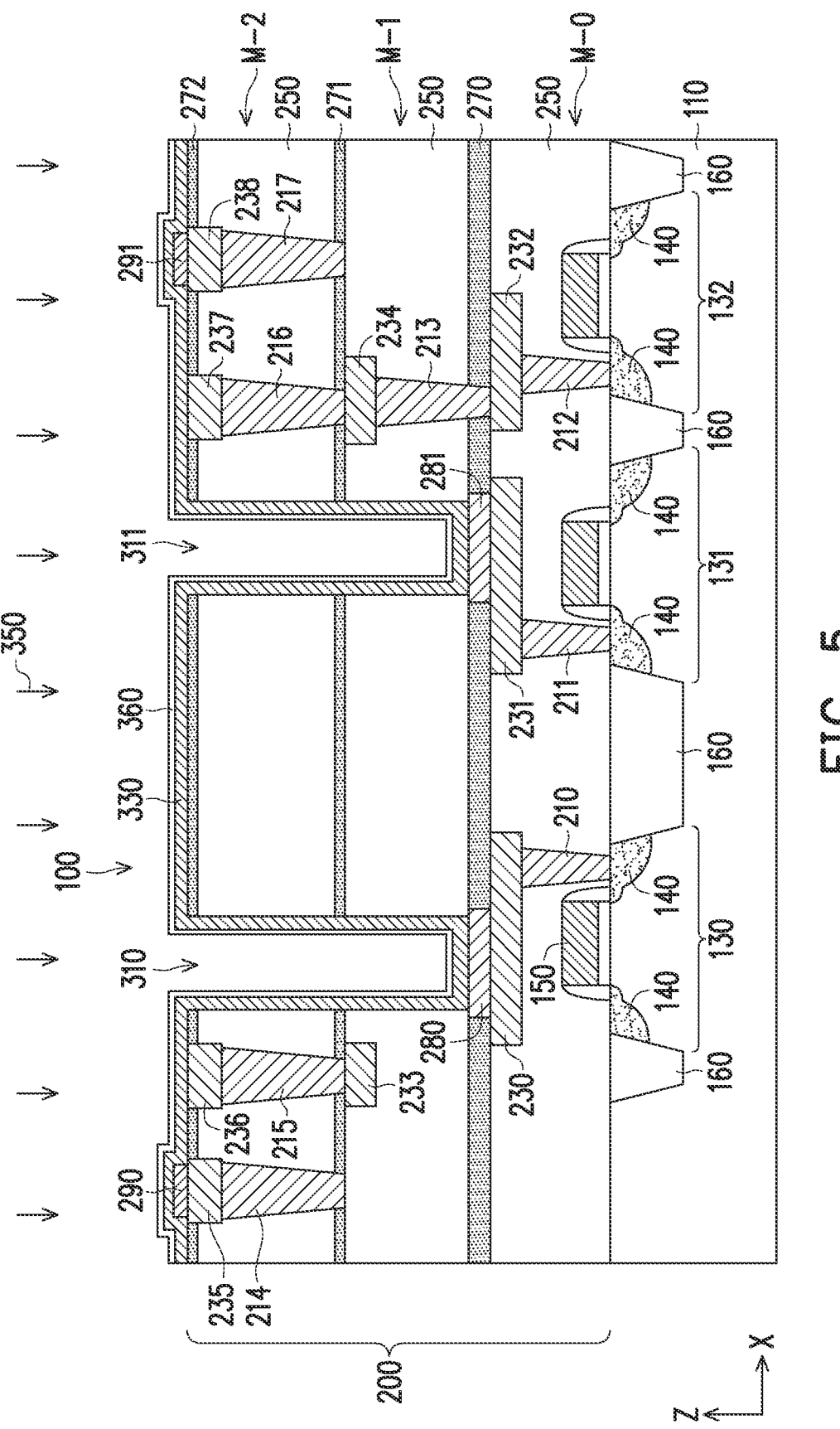

Referring now to FIG. 5, a deposition process 350 is performed to deposit a dielectric layer 360 over the metal compound layer 330. For example, the dielectric layer 360 is formed to partially fill in the trenches 310-311, including on the side surfaces and the bottom surfaces of the metal compound layer 330 in the trenches 310-311. In some embodiments, the deposition process 350 may include an ALD process to accurately control the thickness of the dielectric layer 360. In other embodiments, the deposition process 350 may include a CVD process or a PVD process. The dielectric layer 360 may be formed to have a high-k dielectric material composition, for example hafnium oxide (HfO). In other embodiments, the dielectric layer 360 may include, Zr, Al, Ta, Ti, La, O, N, C, or combinations thereof. It is understood that portions of the dielectric layer 360 will serve as the gate dielectric of the to-be-formed TFTs.

Figure 6:
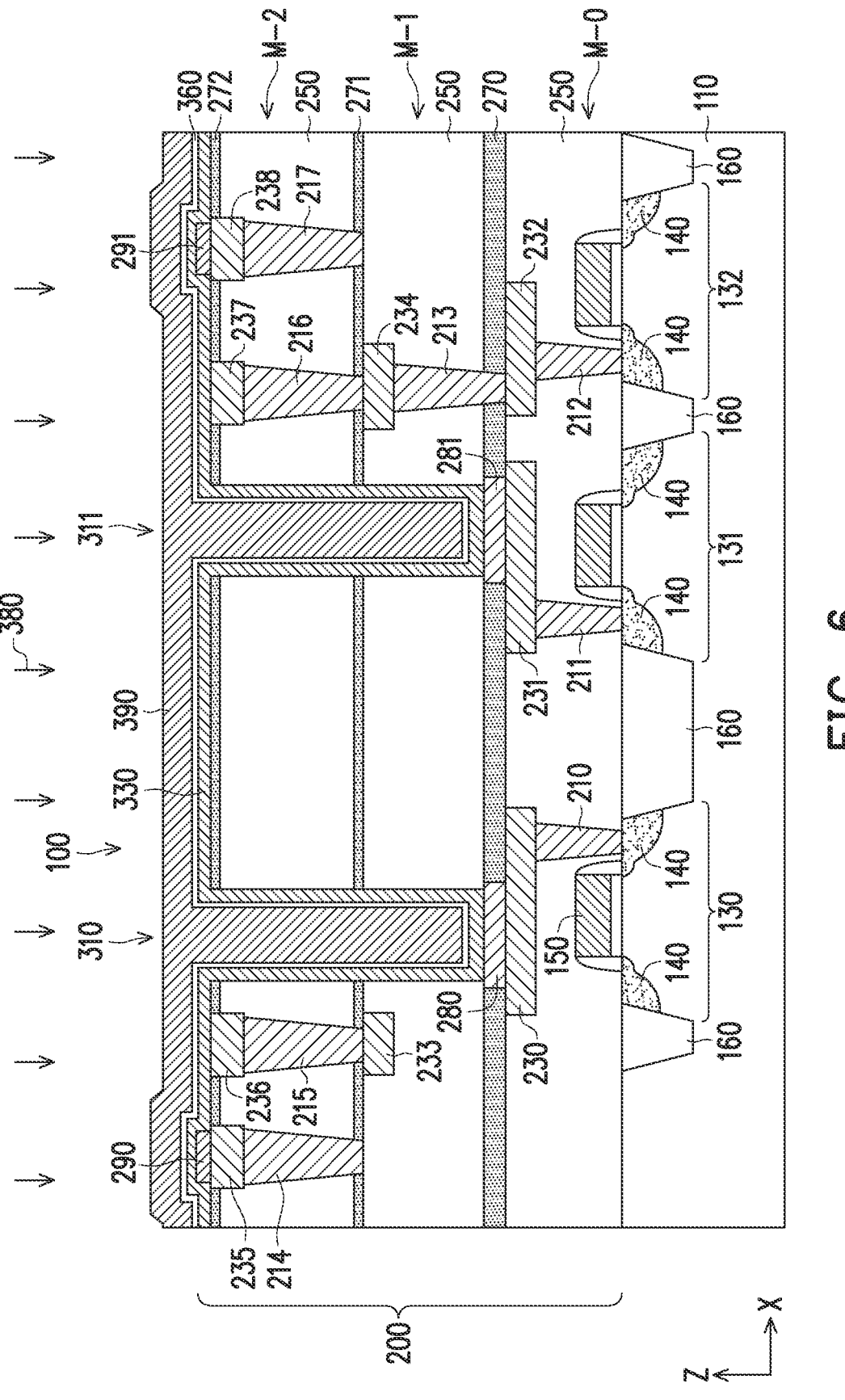

Referring now to FIG. 6, a deposition process 380 is performed to deposit a conductive layer 390 over the exposed upper surfaces of the semiconductor device 100. As shown in FIG. 6, the conductive layer 390 is formed to completely fill in the trenches 310-311, including on the upper surfaces, side surfaces, and the bottom surfaces of the dielectric layer 360. In some embodiments, the deposition process 380 may include an ALD process to accurately control the thickness of the conductive layer 390. In other embodiments, the deposition process 380 may include a CVD process or a PVD process. In some embodiments, the conductive layer 390 may be formed to have a titanium nitride (TiN) material composition. In other embodiments, the conductive layer 390 may include Ti, Ta, W, Mo, Si, O, N, Ni, Co, Ru, Au, Ag, Pt, Mn, Cu, or combinations thereof. It is understood that portions of the conductive layer 390 will serve as the gate electrode of the to-be-formed TFTs.

Figure 7:
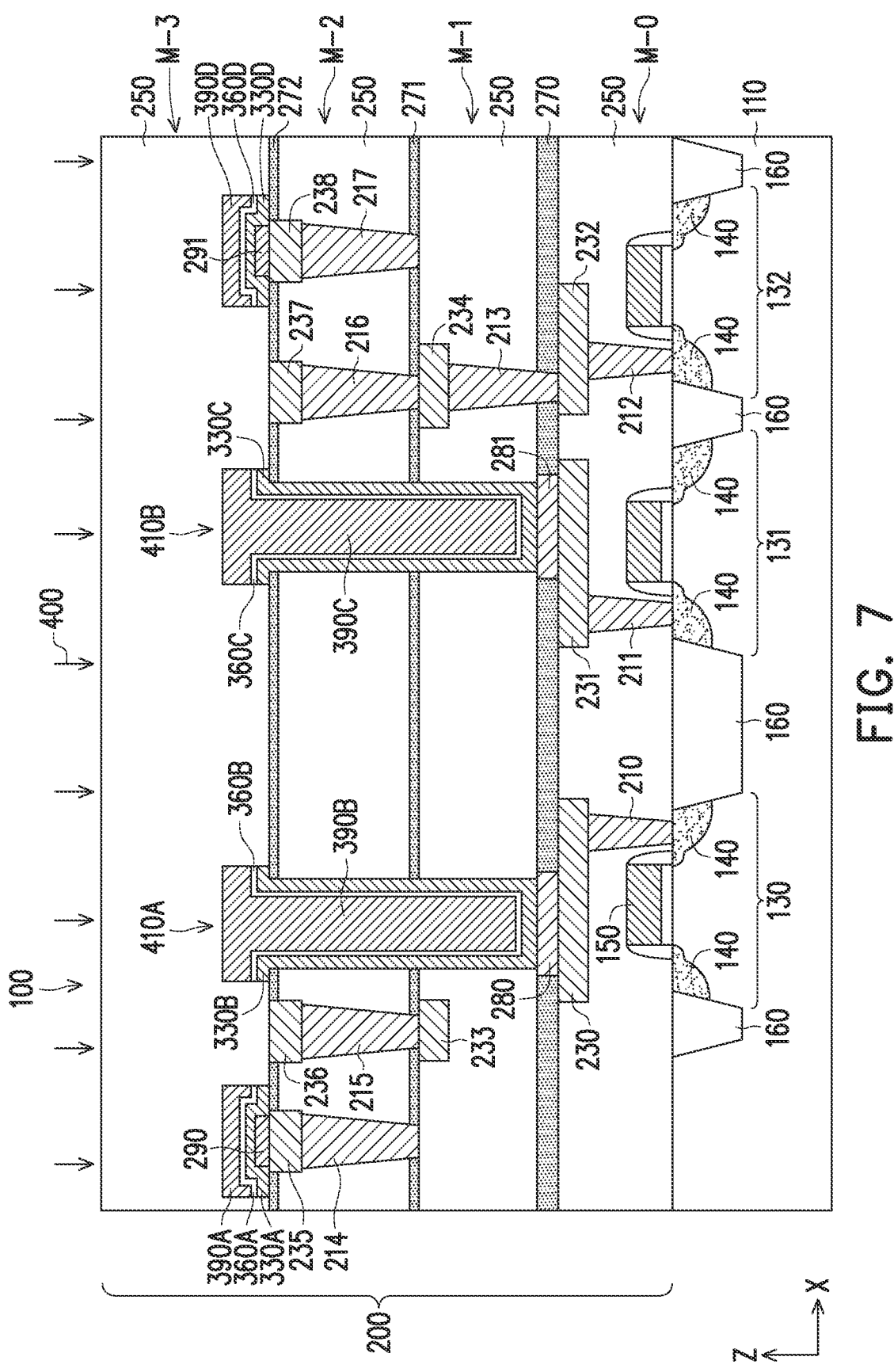

Referring now to FIG. 7, an etching process 400 is performed to break up the conductive layer 390, the dielectric layer 360, and the metal compound layer 330 into separate portions 390A, 390B, 390C, 390D, 360A, 360B, 360C, 360D, 330A, 330B, 330C, and 330D, respectively. Note that the metal compound layer 330B, the dielectric layer 360B, and the conductive layer 390B respectively constitute the channel, the gate dielectric, and the gate electrode of a TFT 410A, and that the metal compound layer 330C, the dielectric layer 360C, and the conductive layer 390C respectively constitute the channel, the gate dielectric, and the gate electrode of a TFT 410B.

A deposition process is then performed to deposit another ILD 250 over the exposed surfaces of the semiconductor device 100, including over the TFTs 410A and 410B. The ILD 250 may serve as the ILD for another metal layer M-3.

Figure 8:
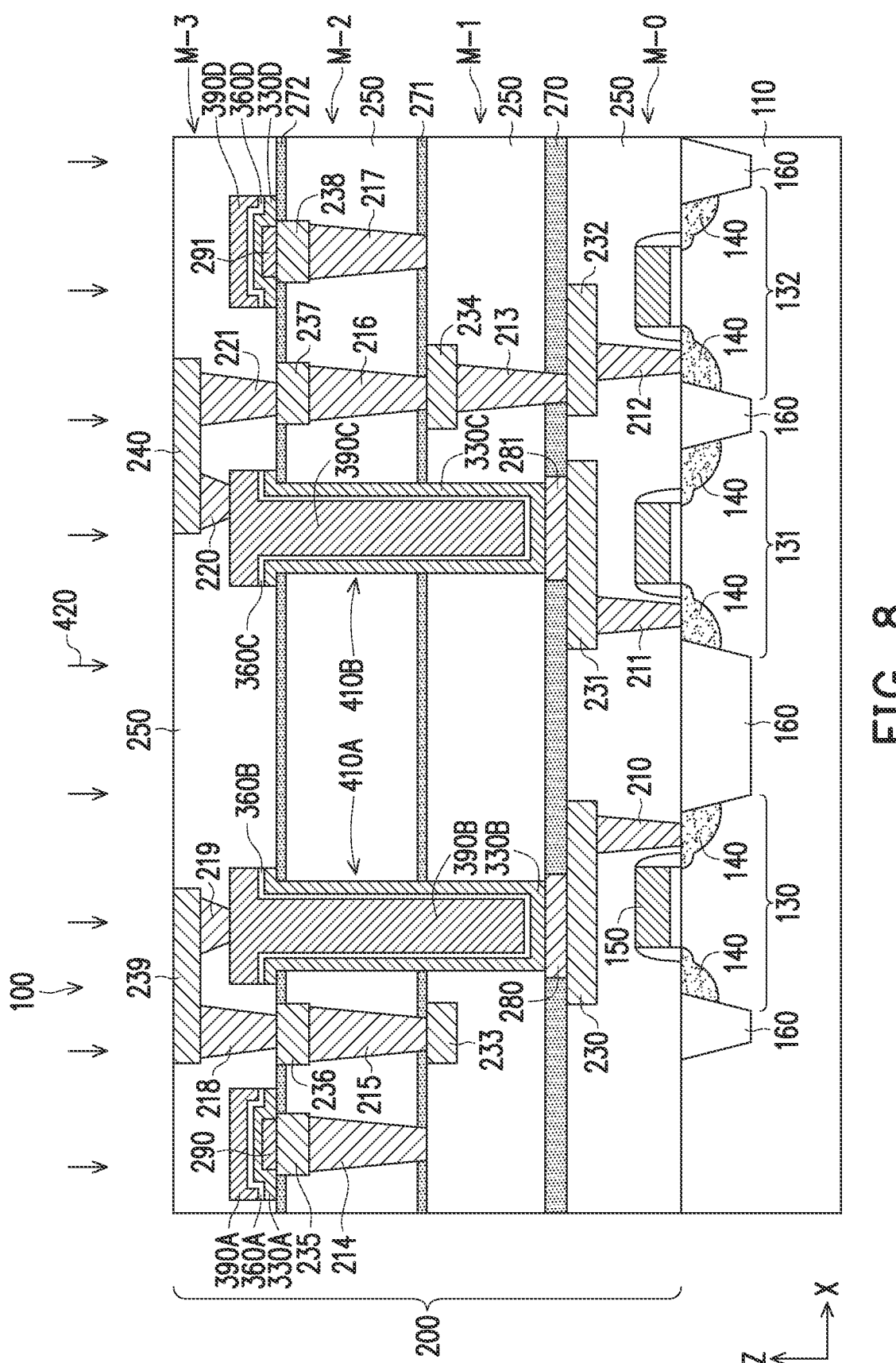

Referring now to FIG. 8, a metal routing process 420 is performed to the semiconductor device 100 to form additional metal routing components of the M-2 layer. For example, vias 218, 219, 229, and 221 may be formed on the upper surfaces of the metal line 236, the conductive layer 390B, the conductive layer 390C, and the metal line 237, respectively. A metal line 239 may be formed over the vias 218 and 219 to electrically connect them together. A metal line 240 may be formed over the vias 220 and 221 to electrically connect them together. The metal lines 239-240 and the vias 218-221 allow for electrical connectivity or electrical access to the TFTs 410A and 410B.

Figure 9:
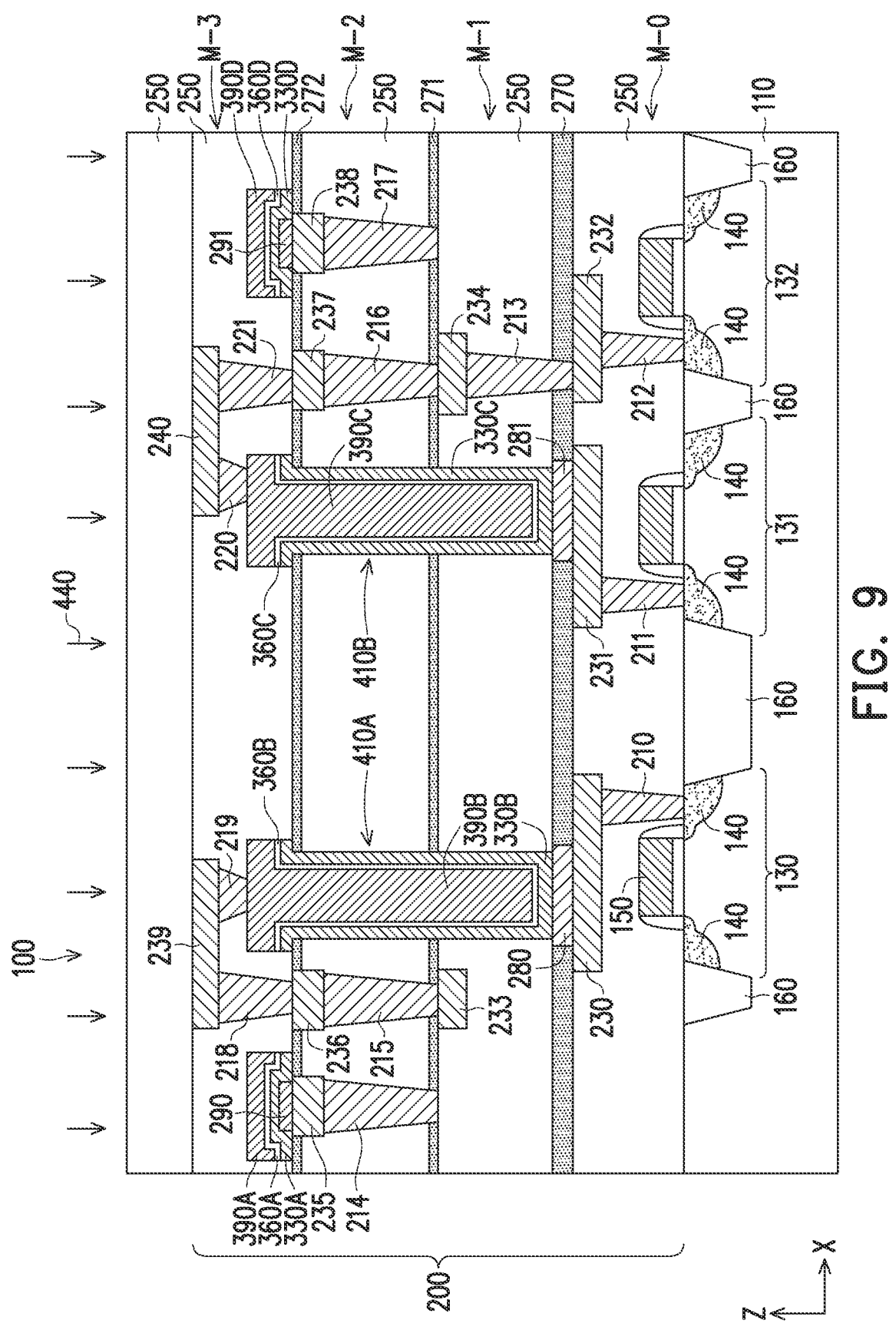

Referring now to FIG. 9, an ILD deposition process 440 is performed to the semiconductor device 100 to form another ILD 250 over the M-3 layer. This ILD 250 may seal and protect the components of the semiconductor device 100 below.

Figure 10:
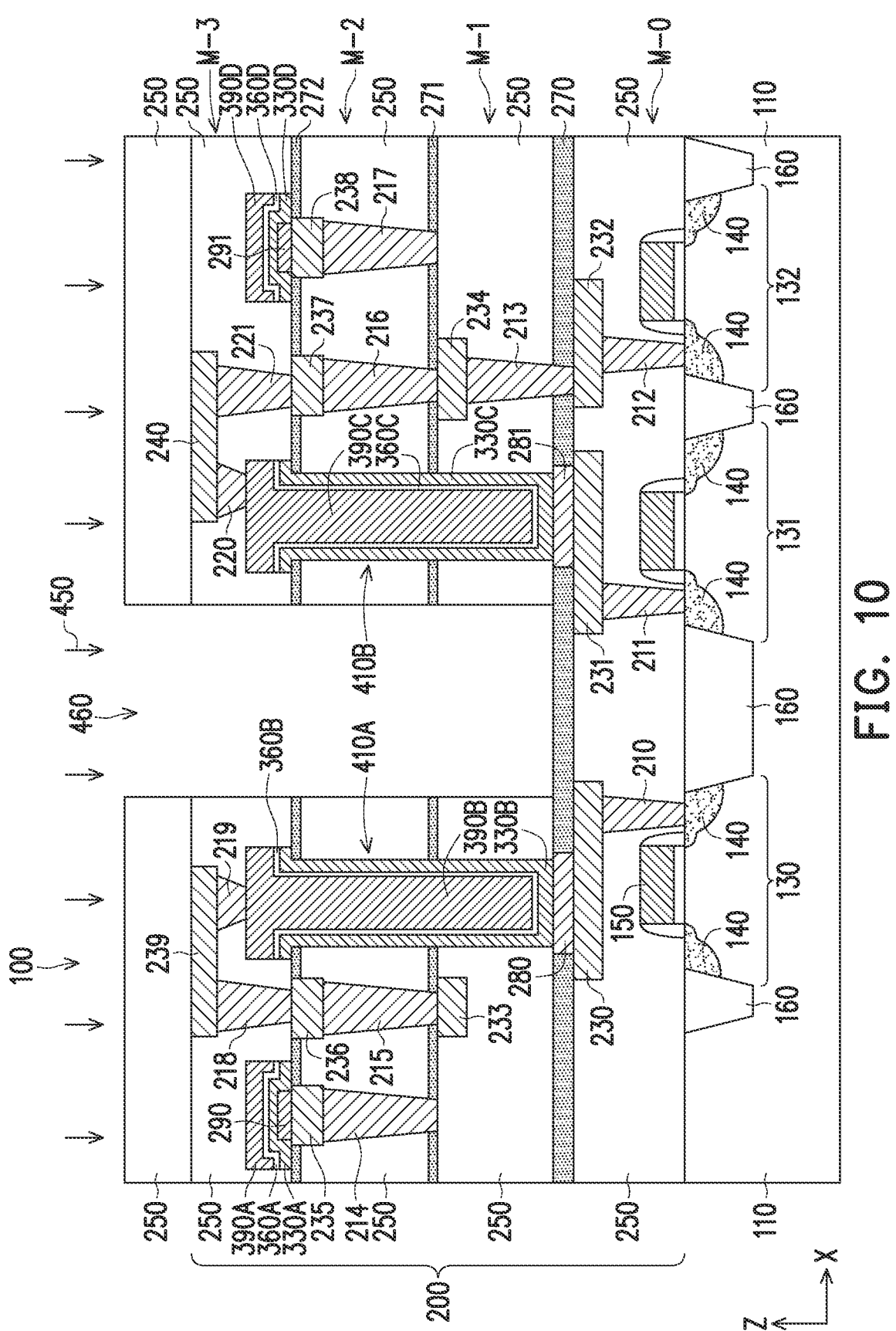

Referring now to FIG. 10, an etching process 450 is performed to the semiconductor device 100 to etch an opening 460. In some embodiments, the etching process 450 includes a dry etching process. In other embodiments, the etching process 450 includes a wet etching process. The opening extends vertically downwards through the interconnect structure 200, including the ILDs 250 of the M-1, M-2, and M-3 layers, but stops at the ESL 270. The opening 460 is formed between the TFT 410A and the TFT 410B. It is understood that the opening 460 may be used to collect a fluid sample (e.g., nasal fluid of a patient) for diagnostic purposes when the semiconductor device 100 is put to actual use.

Figure 11:
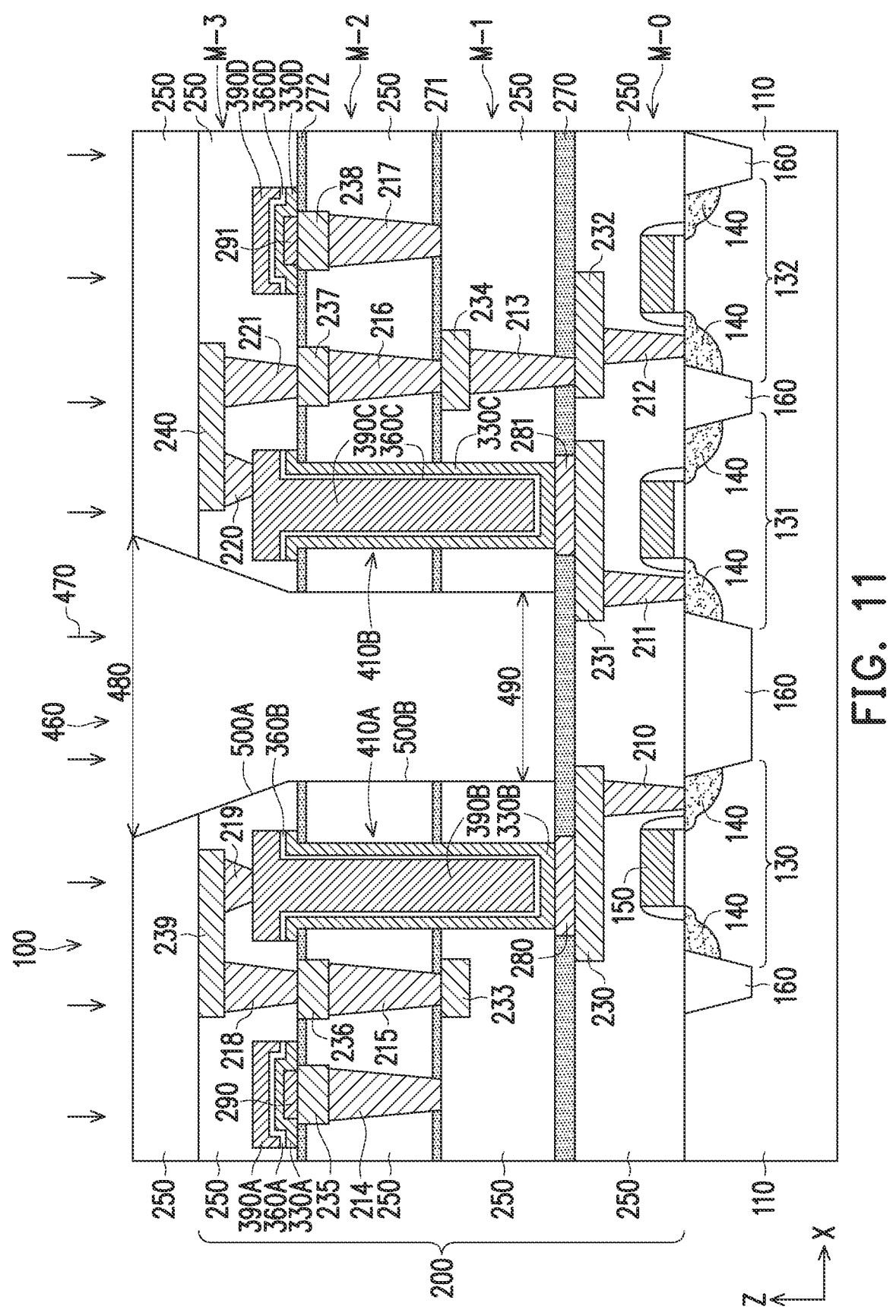

Referring now to FIG. 11, an etching process 470 is performed to the semiconductor device 100 to re-shape the opening 460. In more detail, the opening 460 is re-shaped to have a cross-sectional side view profile that is wider at the top and narrower at the bottom. For example, the top of the opening 460 may have a horizontal dimension 480, and the bottom of the opening 460 may have a horizontal dimension 490, where the horizontal dimension 480 is substantially greater than the horizontal dimension 490.

Another way of describing the re-shaped opening 460 is that its sidewall segments 500A and 500B have different taper angles or different slant angles. As shown in FIG. 11, the sidewall segment 500B is located below the sidewall segment 500A (i.e., closer to the substrate 110 than the sidewall segment 500A). The sidewall segment 500A may have a greater taper angle or slant angle than the sidewall segment 500B. In some embodiments, the sidewall segment 500B is substantially vertical (e.g., oriented along the Z-direction), but the sidewall segment 500A is substantially slanted. It is understood that, although FIG. 11 illustrates the sidewall segments 500A and 500B as being substantially straight or linear (regardless of their respective slant angle), it is not necessarily the case in the actually-fabricated device. In other words, the sidewall segments 500A and/or 500B may be curved or rounded (especially the sidewall segment 500A). Furthermore, the re-shaped opening 460 may include more than two sidewall segments 500A and 500B in alternative embodiments, where the multiple sidewall segments are oriented at different slant angles (e.g., a top sidewall segment oriented with the greatest slant angle, a middle sidewall segment oriented with a smaller slant angle, and a bottom sidewall segment oriented with the smallest slant angle).

In any case, one reason the opening 460 is re-shaped to have a wider horizontal dimension 480 at the top is that such a profile facilitates the collection of the fluid sample in real world use scenarios. Had the opening 460 not been widened at the top, the fluid sample may be trapped at the top and not flow completely through the opening 460. In other words, a narrow dimension at the top of the opening 460 may cause an air bubble to be trapped in the opening 460, which may defeat the purpose of using the opening 460 to collect the fluid sample for analysis. Since the opening 460 has been widened at the top herein, the fluid sample can flow more easily into the opening 460, which gives the semiconductor device 100 a greater exposure to the miniature targets in the fluid. As such, the semiconductor device 100 can function more effectively and more efficiently as a sensor device.

Figure 12:
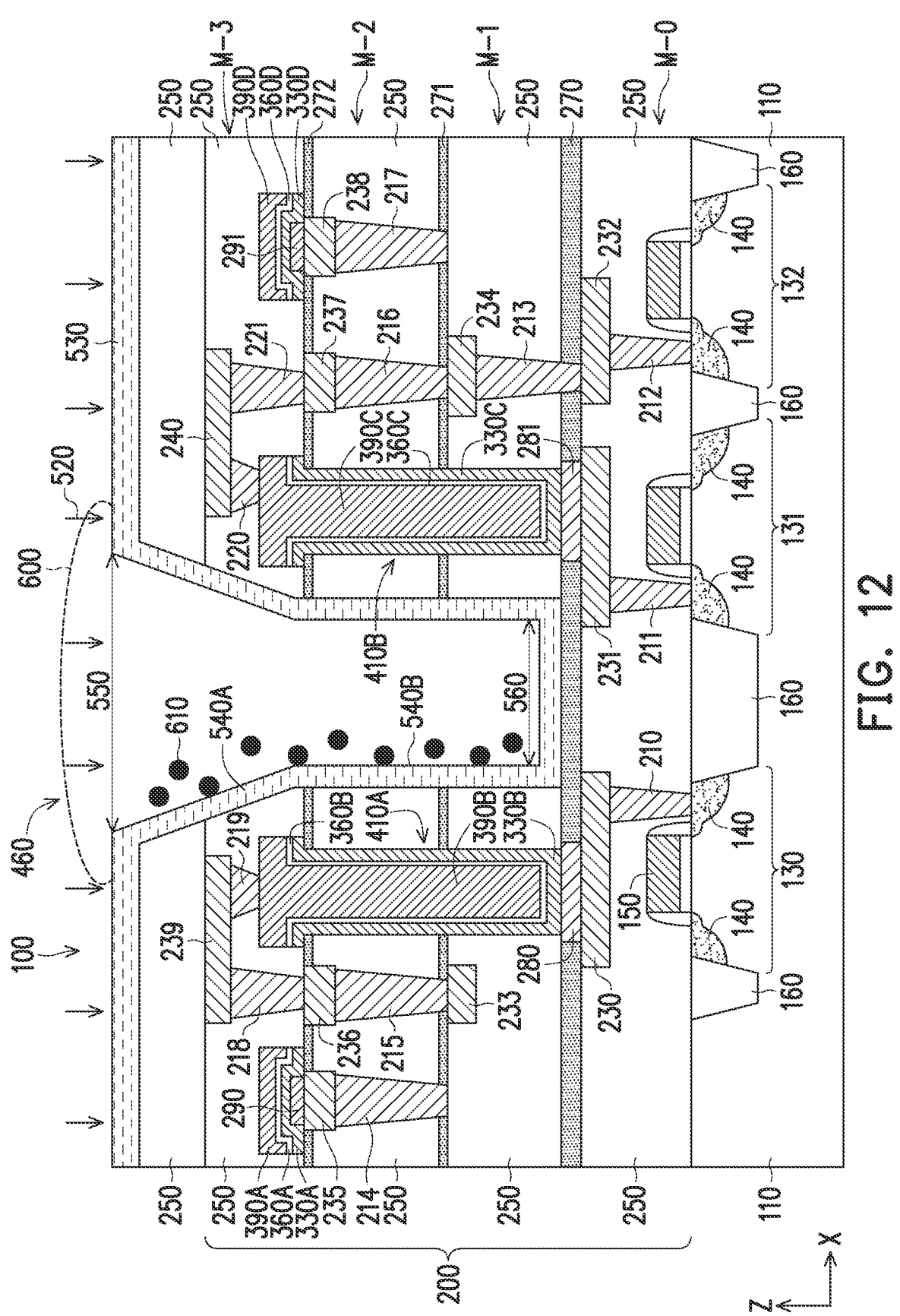

Referring now to FIG. 12, a deposition process 520 is performed to the semiconductor device 100 to form a sensing film 530 over the exposed surfaces of the semiconductor device 100. The deposition process 520 may include a CVD process, a PVD process, or an ALD process. Portions of the sensing film 530 are formed over the upper surfaces of the ILD 250, and other portions of the sensing film 530 are formed to partially fill the opening 460. For example, the portions of the sensing film 530 are formed on bottom surface of the opening 460 (i.e., the upper surface of the ESL 270), as well as on the sidewall segments 500A and 500B.

In embodiments where the deposition process 520 is a conformal deposition process, the deposition process 520 may slightly shrink the size of the opening 460, but its cross-sectional side view profile is substantially maintained. For example, the opening 460 now has sidewall segments 540A and 540B that are substantially similar to the sidewall segments 500A and 500B, respectively. In other words, the sidewall segment 540A is more tapered or slanted than the sidewall segment 540B, and that a horizontal dimension 550 of the opening 460 at the top is substantially greater than a horizontal dimension 560 of the opening 460 at the bottom. In other words, the sidewall segments 540A and 540B substantially inherit the slant angles of the sidewall segments 500A and 500B of FIG. 11, respectively.

In some embodiments, the sensing film 530 may include hafnium oxide, tantalum oxide, zirconium oxide, some other suitable high k dielectric(s), or any combination of the foregoing. In some embodiments, the sensing film 530 may include multiple layers, where at least some of the layers may have different material compositions than the rest of the layers of the sensing film 530.

Regardless of the material composition and/or the number of layers of the sensing film 530, it is understood that the sensing film 530 is configured to facilitate the sensing or detection of predefined miniature targets in a fluid. In more detail, as discussed above, the opening 460 is configured to collect a fluid sample 600 in real world use. For example, the semiconductor device 100 may be a part of nasal swab test for testing whether a patient is infected with the COVID-19 virus. As the user swabs his/her nasal cavity with a nasal swab device, a fluid sample 600 of the nasal fluid of the patient may be collected. The nasal fluid is collected by the opening 460. The fluid sample 600 may contain miniature targets 610, which may be the COVID-19 virus in this simplified example. The miniature targets 610 may have electrical charges, especially when designated antibodies are merged in the fluid sample 600. The material composition of the sensing film 530 is configured such that it is sensitive to a pH of the fluid sample 600, and hence it may react to, or bind with, the miniature targets 510. When this occurs, the surface potential difference at the sensing film 530 changes. The change in the surface potential difference changes a threshold voltage of the TFT 410A through a capacitance coupling mechanism, which may be used to characterize and/or identify the miniature targets 610. For example, the TFT 410B may be biased as a voltage reference device while the TFT 410A serves as a sensing device, so as to induce a formation of a channel. Drain current of the TFT 410A may be sensitive to this and may change accordingly. The miniature targets 610 may be characterized and/or identified by an impedance of the channel and/or by the change in the drain current.

In some embodiments, an electric field is applied from the TFT 410B (i.e., the voltage reference device) to drive the miniature targets 610 (which have charges) away from the TFT 410B and toward the TFT 410A (i.e., the sensing device), which may cause a greater number of the miniature targets 610 to stick onto the portions of the sensing film 530 near the TFT 410A, as shown in FIG. 12. This increases the sensitivity of the TFT 410A, since the TFT 410A may be able to sense the presence of the miniature targets 610 in the fluid sample 600 more easily and/or with greater accuracy. In this manner, the semiconductor device 100 offers an improved signal-to-noise ratio compared to conventional devices, which is one of the advantages of the semiconductor device 100 of the present application. Such an advantage is achieved at least in part through the unique physical design of the semiconductor device 100: the disposition of the fluid-collecting mechanism (i.e., the opening 460) is located directly between the miniature-target sensing device (i.e., the TFT 410A) and the voltage reference device (i.e., the TFT 410B). Such a structure allows the voltage reference device to effectively push the miniature targets 610 in the fluid sample 600 uni-directionally toward the sensing device, which allows a greater number of miniature targets to be picked up by (or bonded to) the portion of the sensing film 530 adjacent to the sensing device. It is noted that such a unique structural features of the present application are inherent results of the unique fabrication process flow discussed above with reference to FIGS. 1-12 (e.g., forming the TFTs 410A and 410B, as well as etching the opening 460 directly between the TFTs 410A and 410B).

Figure 13:
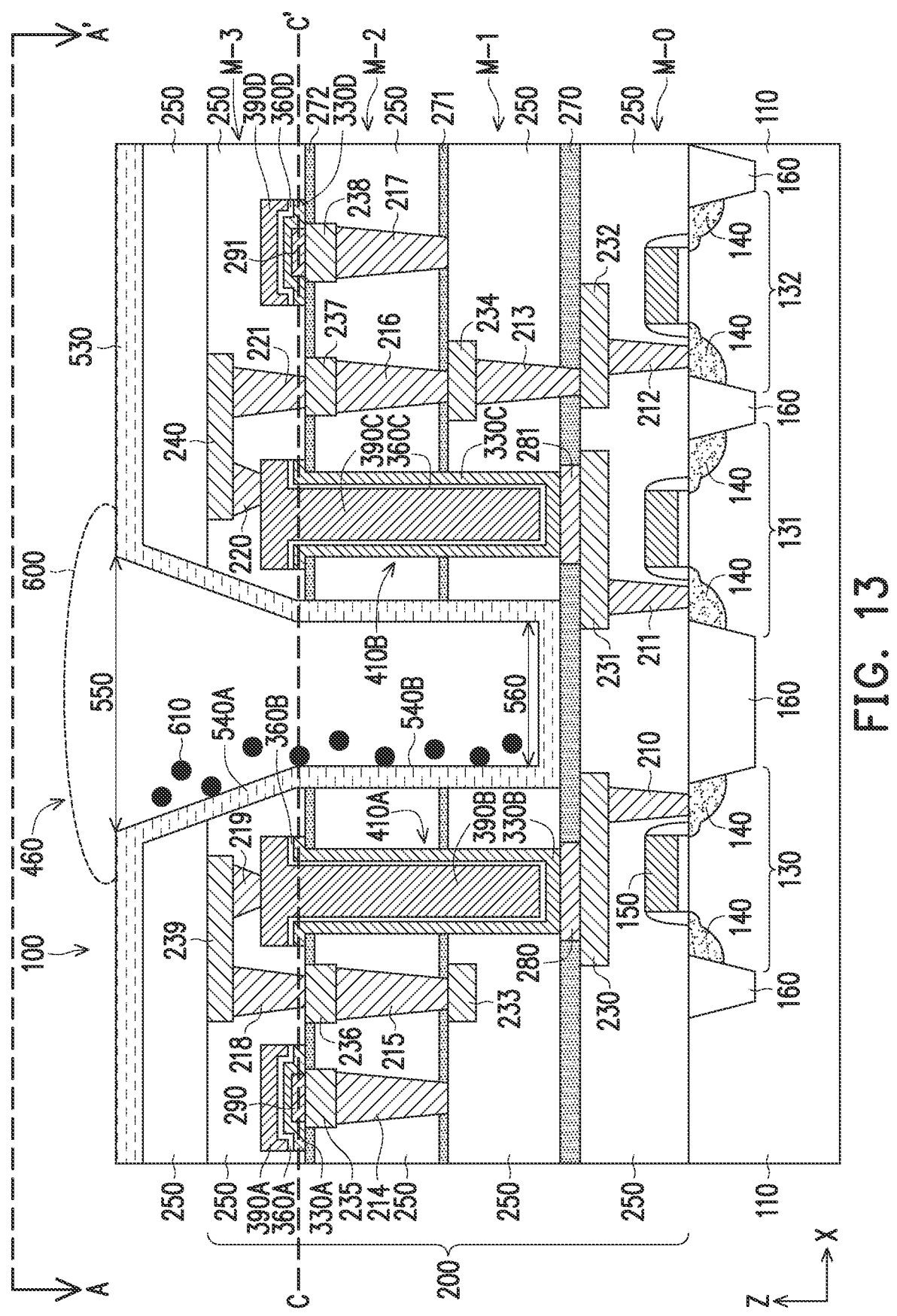

FIG. 13 illustrates an alternative embodiment of the semiconductor device 100. The embodiments of the semiconductor device 100 in FIG. 13 is substantially similar to the embodiment of the semiconductor device 100 in FIG. 12, except that the conductive pads 290 and 291 are no longer formed. That is, in the embodiment shown in FIG. 13, the portions 330A and 330D of the metal compound layer 330 are formed directly on the metal lines 235 and 238, respectively. However, such a change does not substantially affect the intended operation or functionality of the semiconductor device 100.

Figure 14:
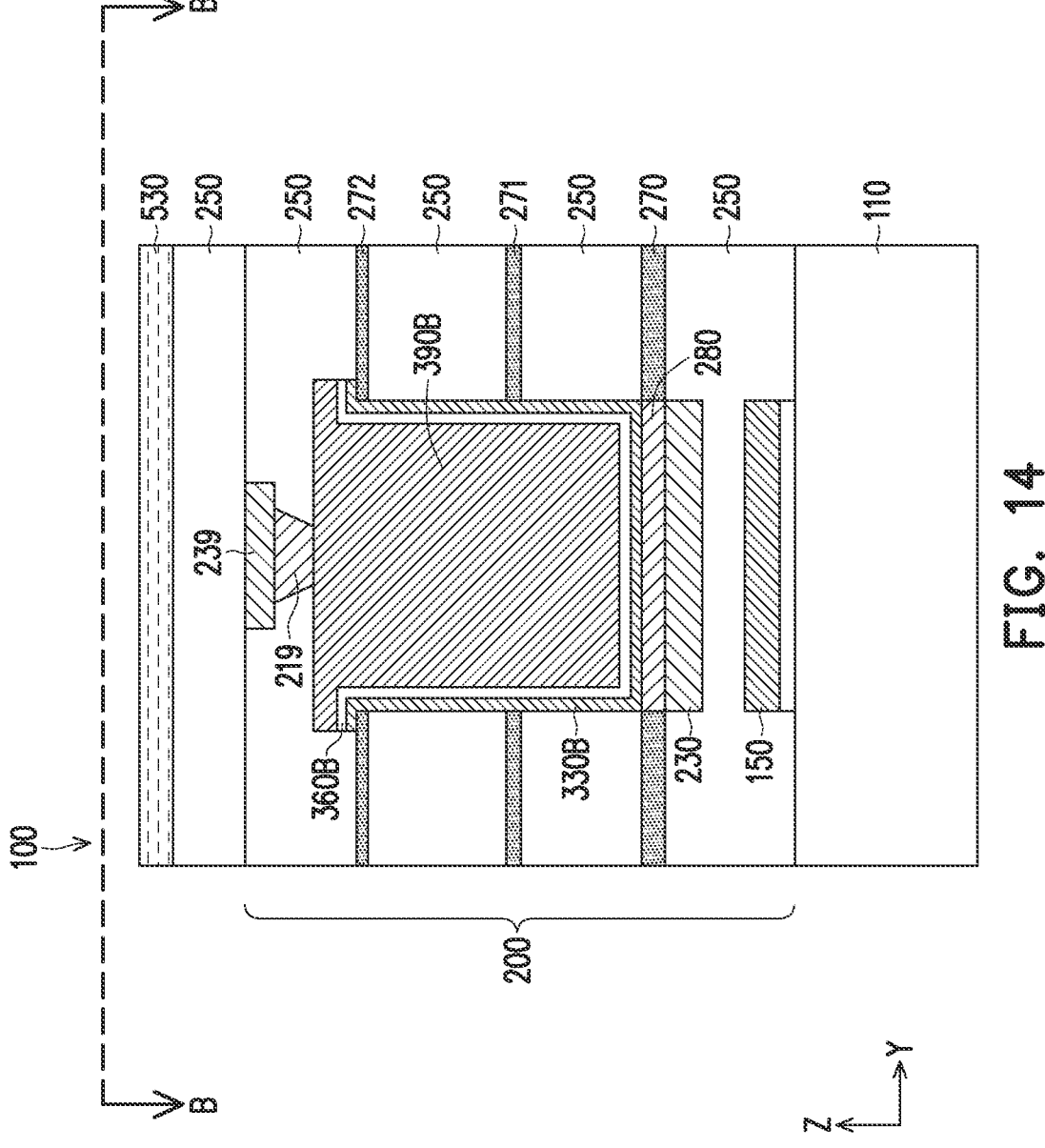
Figure 15:
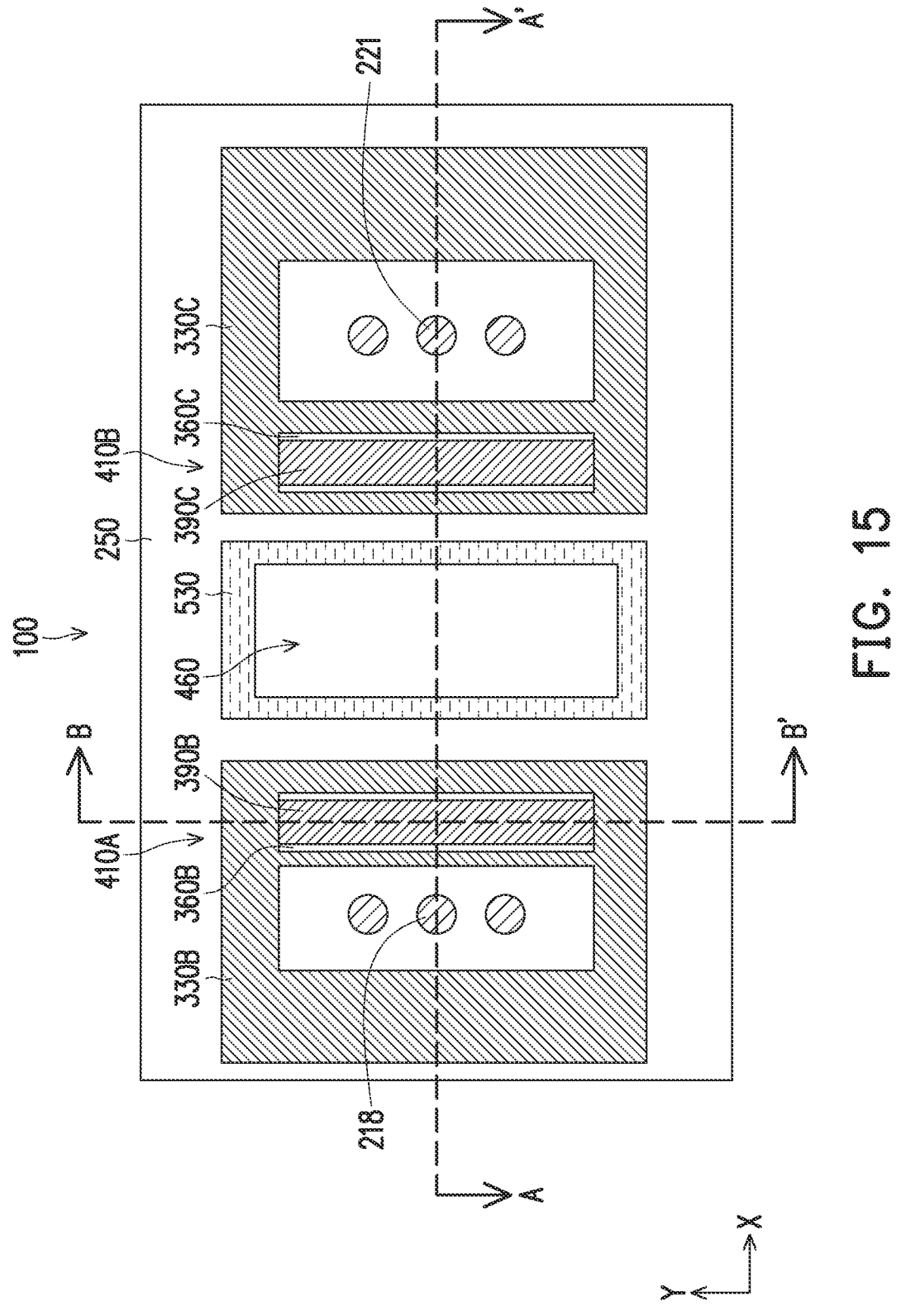
FIG. 15 is a planar top view of a semiconductor device at a stage of fabrication according to various aspects of the present disclosure.
Figure 16:
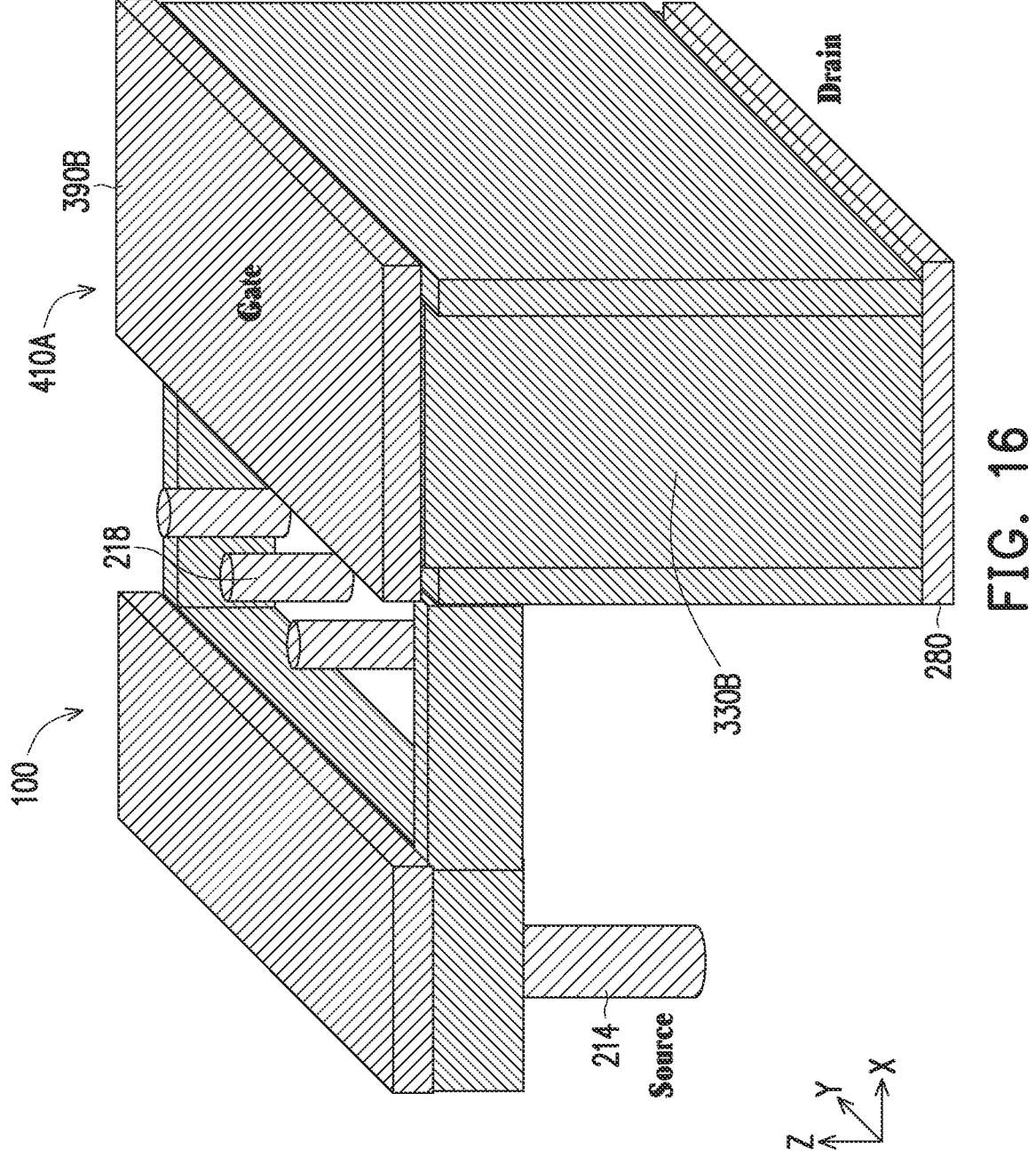
FIG. 16 is a 3-dimensional perspective view of a semiconductor device at a stage of fabrication according to various aspects of the present disclosure.

To facilitate the understanding of the present disclosure, FIGS. 14, 15, and 16 are provided herein to illustrate a Y-cut cross-sectional side view, a planar/top view, and a 3-dimensional perspective view of the semiconductor device 100, respectively. The X-cut cross-sectional side view shown in FIG. 13 corresponds to a cross-section taken along a cutline A-A' in the planar view of FIG. 15. The Y-cut cross-sectional side view shown in FIG. 14 corresponds to a cross-section taken along a cutline B-B' in the planar view of FIG. 15. It is understood that the planar view of FIG. 15 is not taken at the very top (e.g., above the semiconductor device 100), but instead along a cutline C-C' (see FIG. 13) that cuts across the semiconductor device 100. This is done so that the elements of the TFTs 410A and 410B are visible in the top view, including the channel regions (i.e., the metal compound layers 330B/330C), the gate dielectrics (i.e., the dielectric layers 360B/360C), and the gate electrodes (i.e., the conductive layers 390B/390C). Otherwise, these elements of the TFTs 410A and 410B would have been visually obstructed by the sensing film 530 and not directly visible in the planar/top view.

For the sake of simplicity, the 3-dimensional perspective view shown in FIG. 16 illustrates just the TFT 410A portion (i.e., the sensing device) of the semiconductor device 100. Note that the gate dielectric 360B is omitted in FIG. 16 also for reasons of simplicity. The 3-dimensional view of FIG. 16 helps illustrate not just the gate component (i.e., the conductive layer 390B) of the TFT 410A, but also the source and drain components. For example, the conductive pad 280 (also shown in the X-cut view of FIG. 13 and the Y-cut view of FIG. 14) may serve as the drain component of the TFT 410A, while the via 214 (see FIG. 13) may serve as the source component of the TFT 410A. It is also understood that the metal line 235 (see FIG. 13) disposed above the via 214 may also serve as a part of the source component, though the metal line 235 is omitted in FIG. 16 for reasons of simplicity.

Figure 17:
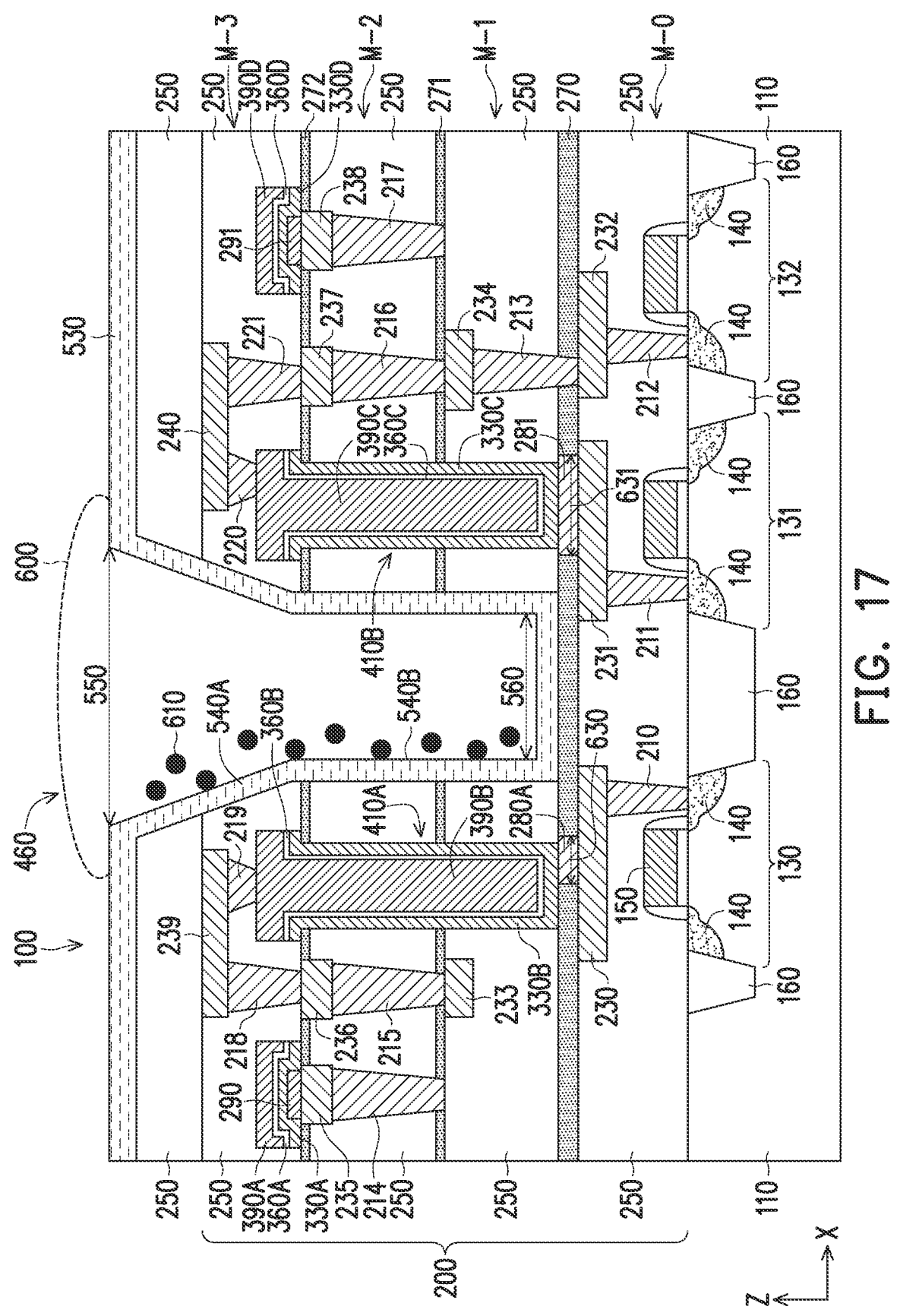
FIG. 17 is a cross-sectional side view of a semiconductor device at a stage of fabrication according to various aspects of the present disclosure.

FIG. 17 illustrates an X-cut cross-sectional side view of another alternative embodiment of the semiconductor device 100. The semiconductor device 100 shown in this alternative embodiment is substantially similar to the embodiments illustrated in FIGS. 12-13, and as such, similar components are labeled the same in FIGS. 12-13 and 17 for reasons of consistency and clarity. One difference is that the conductive pad 280 has been reduced to a smaller size. For example, whereas the conductive pads 280 and 281 may have somewhat similar lateral dimensions (e.g., with 10% of one another) in the embodiments of FIGS. 12-13, the conductive pad 280A now has a lateral dimension 630 that is substantially smaller than a lateral dimension 631 of the conductive pad 281 in the embodiment of FIG. 17, where the lateral dimensions 630 and 631 are each measured in the X-direction. In some embodiments, a ratio of the lateral dimension 630 and the lateral dimension 631 is smaller than 1 and in a range between about 0.5 and about 0.1. Such a range is not randomly chosen but specifically configured to optimize the performance of the TFT 410A. For example, as will be discussed in more detail below, as the dimension 630 shrinks, the drain current sensitivity to the miniature targets 610 is improved. However, if the dimension 630 shrinks too much, then the conductive pad 280A may not be able to adequately serve as the drain of the TFT 410A. The ratio between the dimensions 630:631 above is optimized such that the drain current of the TFT 410A is highly sensitive to the presence of the miniature targets 610, without compromising the efficacy of the conductive pad 280A serving as the drain component of the TFT 410A.

Another way of describing the reduced lateral dimension 630 of the conductive pad 280A is that its upper surface is in direct contact with a portion, but not all, of the metal compound layer 330B. This is because the resized conductive pad 280A is smaller in the X-direction than the bottom surface of the metal compound layer 330B, and therefore it does not come into physical contact with the entire bottom surface of the metal compound layer 330B. In contrast, the conductive pad 281 may be larger than the bottom surface of the metal compound layer 330C in the X-direction and may come into physical contact with an entirety of the bottom surface of the metal compound layer 330C.

One reason for the shrinking of the conductive pad 280A is to improve the drain current sensitivity (or signal-to-noise ratio) of the semiconductor device. To illustrate this concept, refer now to FIG. 18A, which illustrate a 3-dimensional perspective view of the TFT 410A according to the embodiment of FIGS. 12-13, as well as FIG. 18B, which illustrate a 3-dimensional perspective view of the TFT 410A according to the embodiment of FIG. 17. In other words, FIG. 18A corresponds to the embodiment where the conductive pad 280 has not been reduced in size, but FIG. 18B corresponds to the embodiment where the conductive pad 280A has been reduced in size. The approximate locations of the gate, source, and drain for the TFT 410A are labeled in FIGS. 18A and 18B to facilitate the ensuing discussions. Note that the drain of the TFT 410A in FIGS. 18A and 18B corresponds to the conductive pad 280 and the conductive pad 280A, respectively.

Figures 18A, 18B:
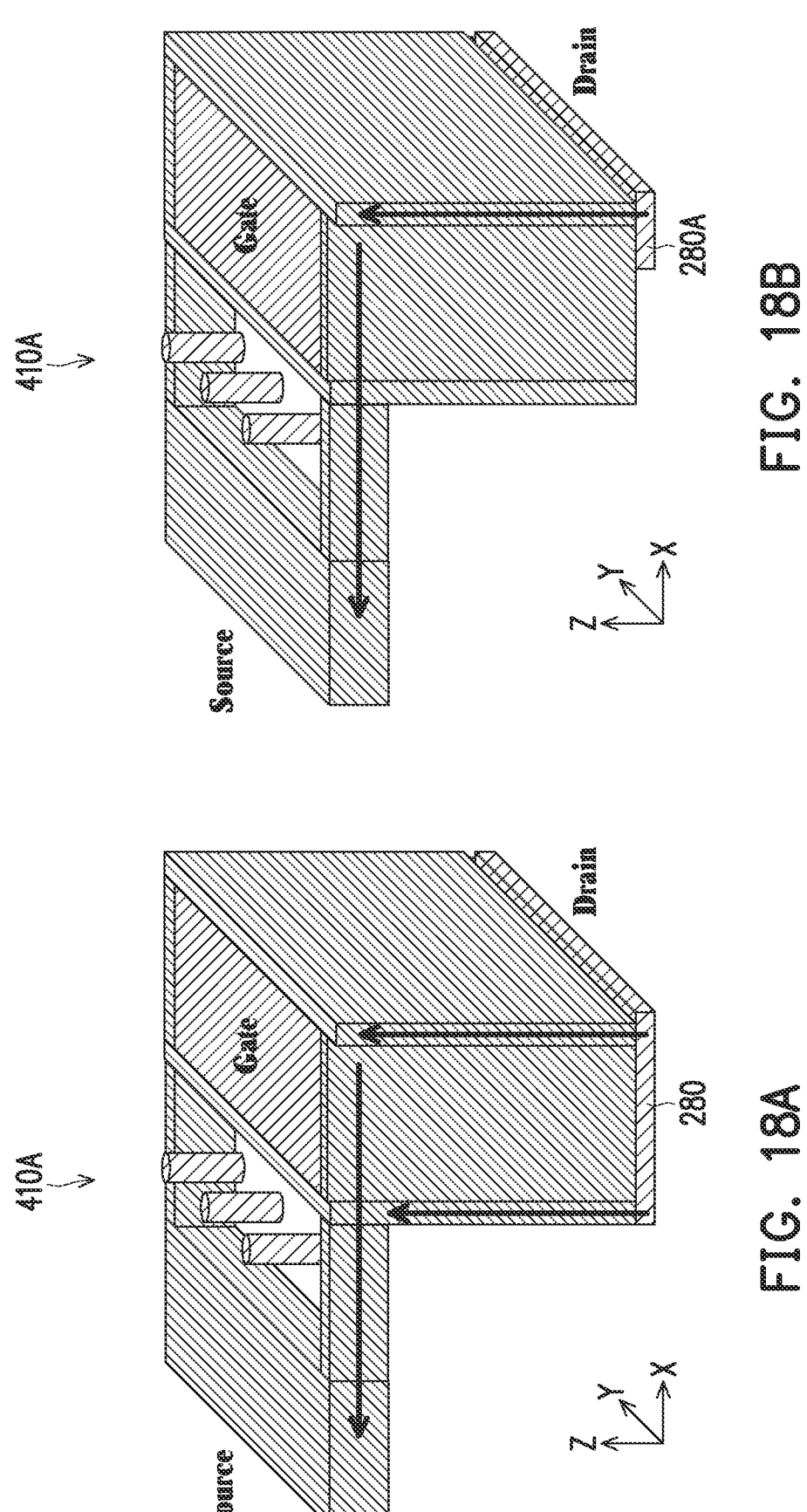
FIGS. 18A-18B each illustrate a 3-dimensional perspective view of a semiconductor device at a stage of fabrication according to various aspects of the present disclosure.

The drain current of the TFT 410A is visually illustrated as the arrows in FIGS. 18A-18B and flows from the drain to the source. Since the conductive pad 280 is larger (in the X-direction) in the embodiment of FIG. 18A, the drain current spans across a relatively wide range, which is represented herein by the two vertical arrows that point upwardly from the drain toward the gate in FIG. 18A. As discussed above, the opening 460 is located to the "right" of the TFT 410A in the X-direction (see FIG. 17), and the miniature targets 610 to be sensed are attached to the portion of the sensing film 530 that is located to the "right" of the TFT 410A. As such, the closer the drain current (or the path thereof) is to the opening 460, the more sensitive it is to the presence of the miniature targets 610. However, since the drain current in the embodiment of FIG. 18A is spread out across a substantial entirety of the drain, much of the drain current is not as sensitive to the miniature targets 610 as it could have been. Alternatively stated, the sensing of the miniature targets 610 is dominated by the rightmost portion of the drain current (e.g., represented by the vertical arrow on the right), but the leftmost portion of the drain current (e.g., represented by the vertical arrow on the left) does not contribute much to the sensing of the miniature targets 610. However, the rightmost portion of the drain current is only a small portion of the total drain current, and thus the sensitivity of the TFT 410 of the embodiment of FIG. 18A is not as high as it could have been.

In comparison, the size of the drain (e.g., the conductive pad 280A) has been reduced in the embodiment of FIG. 18B. As such, the drain current spans across a relatively narrow range, which is represented by the single vertical arrow that points upwardly from the drain toward the gate in FIG. 18B. The size-reduced drain is also located at the right of the TFT 410A (e.g., near the opening 460), and thus the drain current flows mostly along the right side of the TFT 410A, which is close to the miniature targets 610 collected in the opening 460. Accordingly, the sensitivity of the TFT 410A is improved, since very little of the drain current is "wasted" in the embodiment of FIG. 18B.

It is understood that the size reduction of the drain need not be applied to the TFT 410B. This is because the TFT 410B serves as the voltage reference transistor, and whether the path of its drain current is located close to the miniature targets 610 or not will have little to no impact on the actual sensing or detection of the miniature targets 610. Therefore, the conductive pad 281 (serving as the drain of the TFT 410B) may have substantially identical sizes in the embodiments 12-13 and 17.

The reduced size of the conductive pad 280A compared to the conductive pad 281 is a unique physical characteristic of the embodiment of FIG. 17. In other words, in addition to offering the other unique physical characteristics discussed above with reference to the embodiments of FIGS. 12-13, the embodiment of FIG. 18 also offers the unique physical characteristic of having a smaller drain for the miniature-target sensing transistor (i.e., the TFT 410A) than the voltage reference transistor (i.e., the TFT 410B). Such a unique physical characteristic is achieved as an inherent result of the unique fabrication process flow, for example, by forming a smaller conductive pad 280A and a larger conductive pad 281 before the rest of the TFT components are formed.

Figure 19:
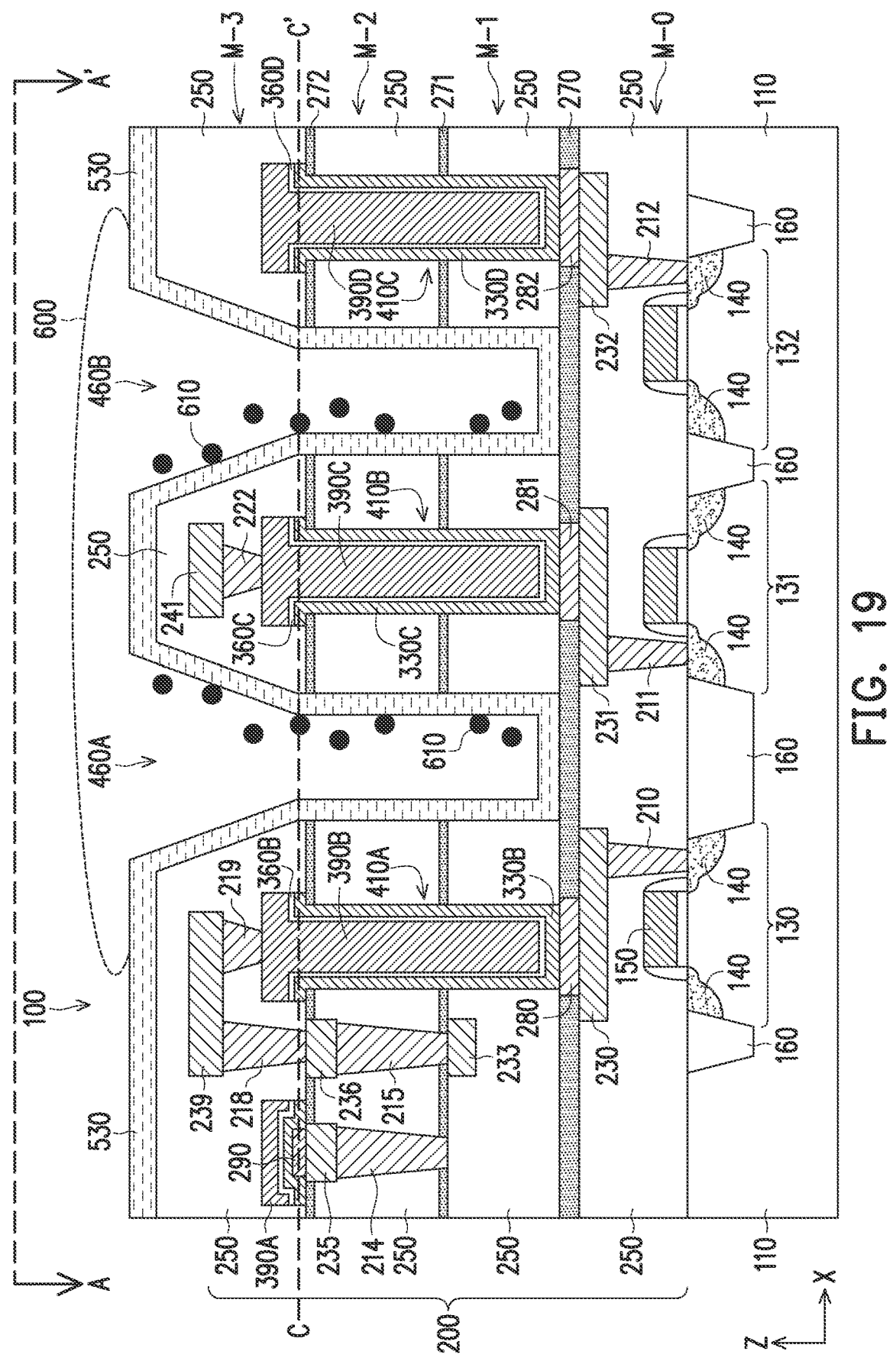
FIG. 19 is a cross-sectional side view of a semiconductor device at a stage of fabrication according to various aspects of the present disclosure.
Figure 20:
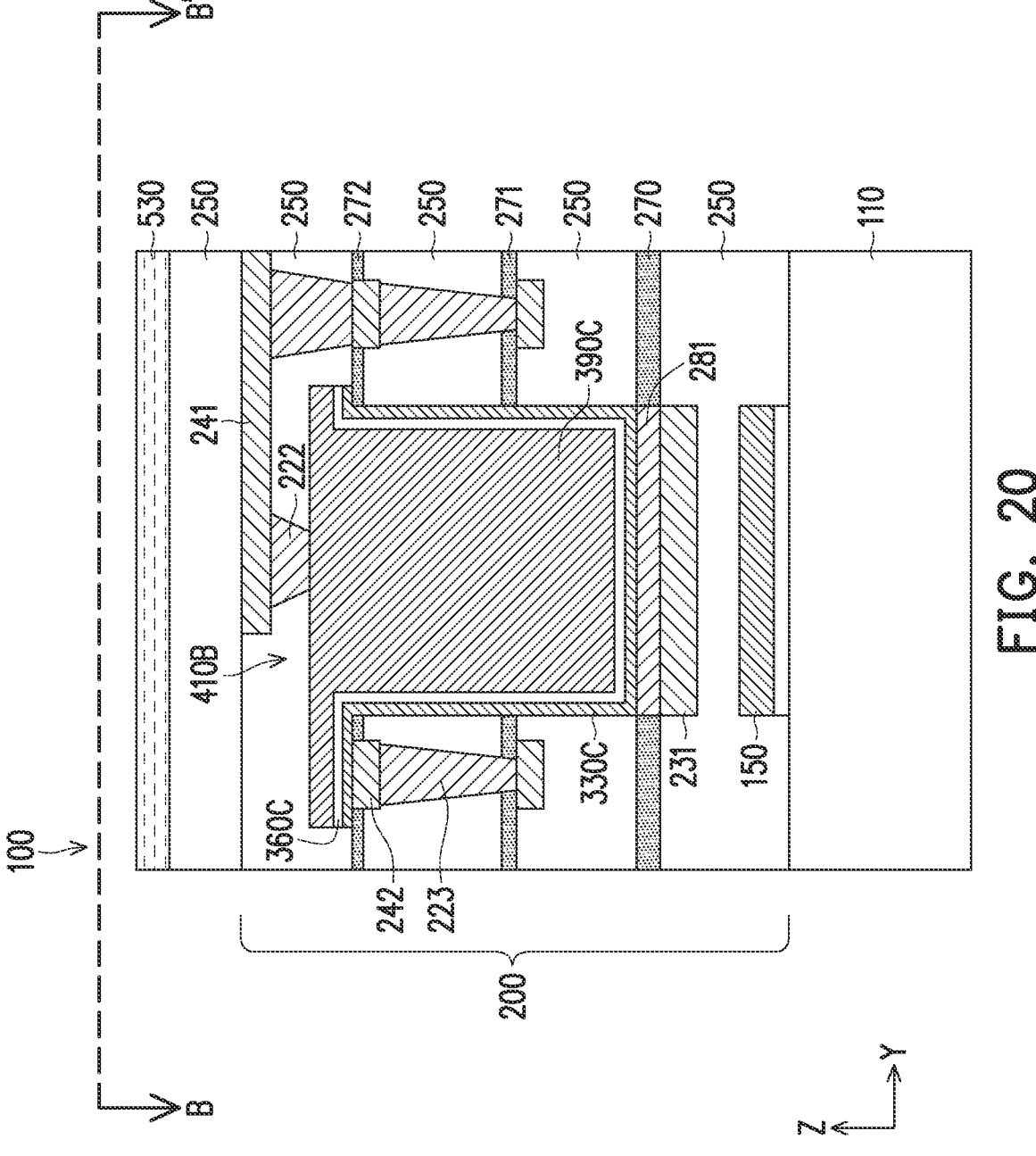
FIG. 20 is a cross-sectional side view of a semiconductor device at a stage of fabrication according to various aspects of the present disclosure.
Figure 21:
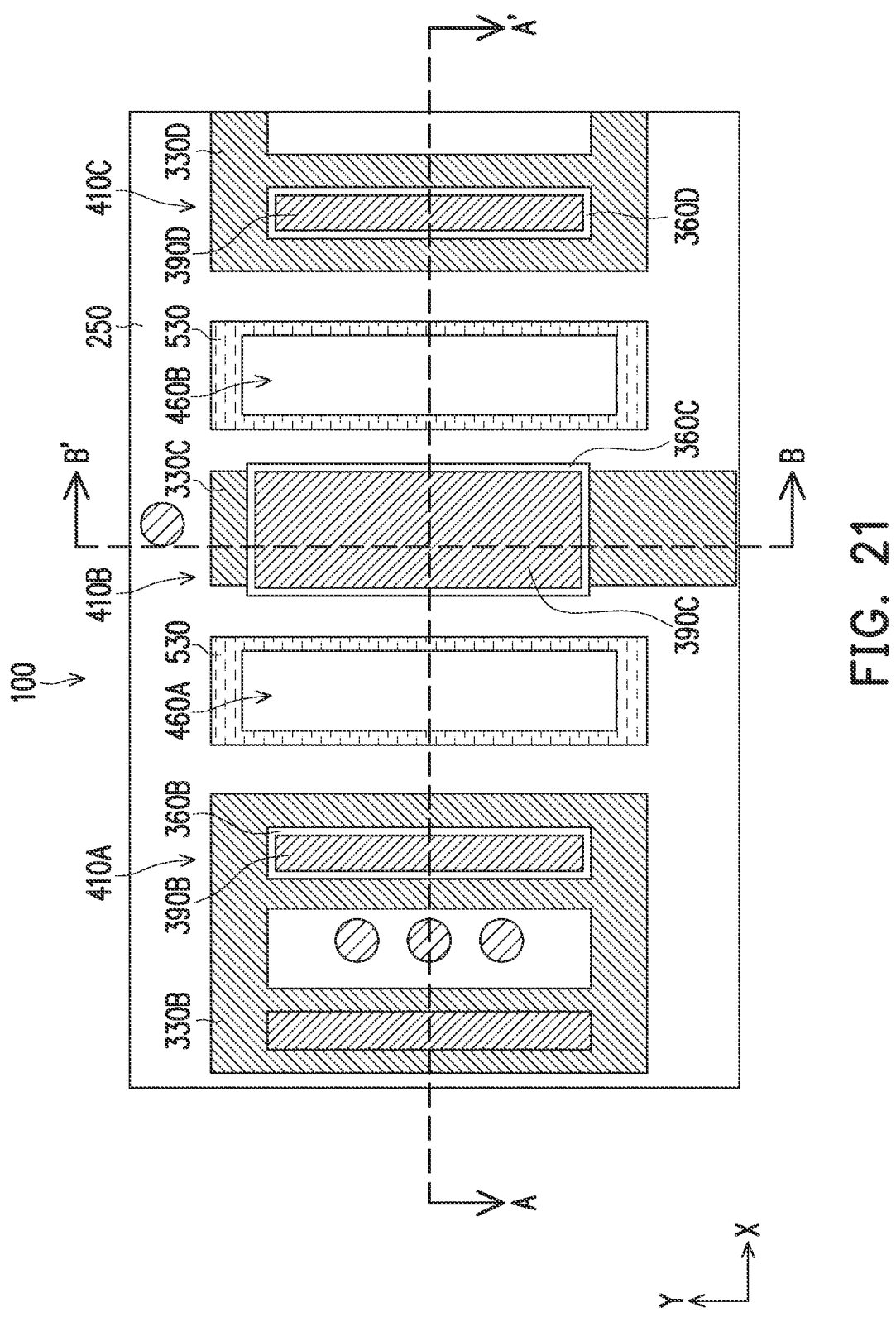
FIG. 21 is a planar top view of a semiconductor device at a stage of fabrication according to various aspects of the present disclosure.

FIGS. 19-22 illustrate yet another embodiment of the semiconductor device 100. FIGS. 19, 20, 21, and 22 are provided herein to illustrate an X-cut cross-sectional side view, Y-cut cross-sectional side view, a planar/top view, and a partial 3-dimensional perspective view of the semiconductor device 100, respectively. The X-cut cross-sectional side view shown in FIG. 19 corresponds to a cross-section taken along a cutline A-A' in the planar view of FIG. 21. The Y-cut cross-sectional side view shown in FIG. 20 corresponds to a cross-section taken along a cutline B-B' in the planar view of FIG. 21. It is understood that the planar view of FIG. 21 is not taken at the very top (e.g., above the semiconductor device 100), but instead along a cutline C-C' (see FIG. 19) that cuts across the semiconductor device 100. This is done so that the elements of the TFTs 410A-410C are visible in the top view, including the channel regions (i.e., the metal compound layers 330B/330C/330D), the gate dielectrics (i.e., the dielectric layers 360B/360C/360D), and the gate electrodes (i.e., the conductive layers 390B/390C/390D). Otherwise, these elements of the TFTs 410A-410C would have been obstructed by the sensing film 530 and not directly visible in the planar/top view. Again, for reasons of consistency and clarity, similar components appearing in the embodiments of FIGS. 12-13 and FIGS. 19-22 will be labeled the same.

Once difference is that the TFT 410B is used herein as the miniature-target sensing transistor, and the TFT 410A is used herein as one of the voltage reference transistors. In other words, there need not be underlying structural differences between the miniaturing-target sensing transistor and the voltage reference transistor (except in the embodiment of FIG. 18 discussed above). By applying different voltages to the different TFTs 410A and 410B (or biasing them differently), the roles of a miniature-target sensing transistor and voltage reference transistor may be switched. Note that electrical access to the TFT 410B may be gained through the via 222 and the metal line 241 disposed above the conductive layer 390C (i.e., the gate electrode of the TFT 410B).

Another difference is that the embodiment of FIGS. 19-22 has a 2-to-1 ratio of voltage reference transistors to miniature-target sensing transistors. In other words, whereas the embodiments of FIGS. 12-13 have one voltage reference transistor for each miniature-target sensing transistor, the embodiment of FIGS. 19-22 implements two voltage reference transistors (e.g., the TFT 410A and the TFT 410C) for each miniature-target sensing transistor (e.g., the TFT 410B). Multiple openings 460A and 460B are also implemented to collect the fluid sample 600 that contains the miniature targets 610. For example, the opening 460A is disposed between the TFT 410A (serving as a voltage reference transistor) and the TFT 410B (serving as miniature-target sensing transistor), and the opening 460B is disposed between the TFT 410C (serving as another voltage reference transistor) and the TFT 410B (again serving as miniature-target sensing transistor). By biasing the TFTs 410A-410C differently, the miniature targets 610 in the opening 460A are driven to the "right" sidewall of the opening 460A, and the miniature targets 610 in the opening 460B are driven to the "left" sidewall of the opening 460B. In this manner, the miniature targets 610 in both of the openings 460A and 460B are driven to be as close to the miniature-target sensing transistor (i.e., the TFT 410B) as possible, so as to enhance the sensitivity of the semiconductor device 100.

Figure 22:
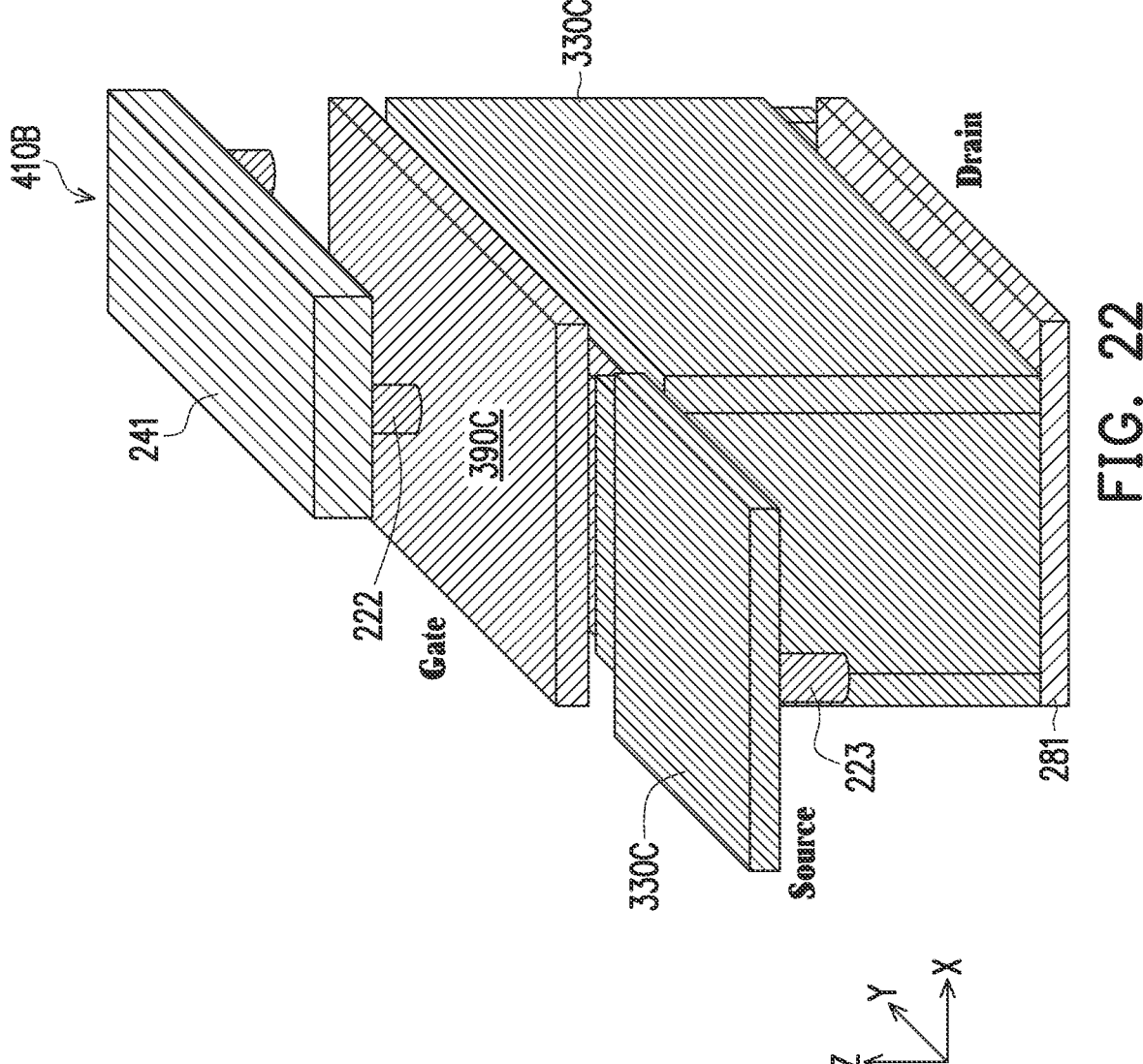
FIG. 22 is a 3-dimensional perspective view of a semiconductor device at a stage of fabrication according to various aspects of the present disclosure.

Another feature of the embodiment of FIGS. 19-22 is that the source of the TFT 410B is not directly visible in the X-cut cross-sectional view of FIG. 19, though it is visible in the Y-cut cross-sectional view of FIG. 20, as well as in the 3-dimensional perspective view of FIG. 22. For example, the metal line 242 and the via 223 disposed below the metal compound layer 330C may serve as the source of the TFT 410B. The gate electrode, the channel, and the drain of the TFT 410B are still served by the conductive layer 390C, the metal compound layer 330C, and the conductive pad 281, respectively. Note that the gate dielectric 360C is omitted in FIG. 22 for reasons of simplicity.

FIG. 23 is a flowchart illustrating a method 800 of fabricating a semiconductor device according to embodiments of the present disclosure. The method 800 includes a step 810 to form an interconnect structure over a semiconductor substrate. The interconnect structure includes a plurality of interconnect layers containing respective vias and metal lines.

The method 800 includes a step 820 to etch a first trench and a second trench in the interconnect structure.

The method 800 includes a step 830 to deposit a metal compound layer in the first trench and the second trench. In some embodiments, the depositing the metal compound layer includes depositing Indium-Gallium-Zinc-Oxide (IGZO) as the metal compound layer.

The method 800 includes a step 840 to deposit a dielectric layer over the metal compound layer. The dielectric layer partially fills the first trench and the second trench. In some embodiments, the depositing the dielectric layer includes depositing hafnium oxide as the dielectric layer.

The method 800 includes a step 850 to deposit a conductive layer over the dielectric layer. In some embodiments, the depositing the conductive layer includes depositing titanium nitride (TiN) as the conductive layer. The conductive layer completely fills the first trench and the second trench. A first thin-film transistor (TFT) is partially formed by portions of the conductive layer, the dielectric layer, and the metal compound layer filling the first trench. A second TFT is partially formed by portions of the conductive layer, the dielectric layer, and the metal compound layer filling the second trench.

The method 800 includes a step 860 to etch an opening that downwardly extends at least partially through the interconnect structure. The opening is formed between the first TFT and the second TFT.

The method 800 includes a step 870 to deposit a sensing film in the opening.

In some embodiments, the semiconductor substrate is a bulk silicon wafer on which at least a first non-TFT and a second non-TFT are formed. In some embodiments, the forming the interconnect structure includes forming a first subset of vias and metal lines and a second subset of vias and metal lines in a first interconnect layer of the interconnect structure. The first subset of vias and metal lines are electrically coupled to the first non-TFT. The second subset of vias and metal lines are electrically coupled to the second non-TFT. The first TFT is electrically coupled to the first non-TFT at least in part through the first subset of vias and metal lines. The second TFT is electrically coupled to the second non-TFT at least in part through the second subset of vias and metal lines.

It is understood that the method 800 may include further steps performed before, during, or after the steps 810-870. For example, the method 800 may include steps of, before the sensing film is deposited: reshaping the opening such that each side surface of the opening includes a first segment and a second segment below the first segment. The first segment has a more tapered profile in a cross-sectional side view than the second segment. As another example, the method 800 may include a step of collecting a fluid in the opening, wherein the fluid contains miniature targets, as well as steps of electrically biasing the first TFT and the second TFT to different voltages, wherein the miniature targets are driven away from the first TFT and toward the second TFT as a result of the electrically biasing. For reasons of simplicity, other additional steps are not discussed herein in detail.

Figure 24:
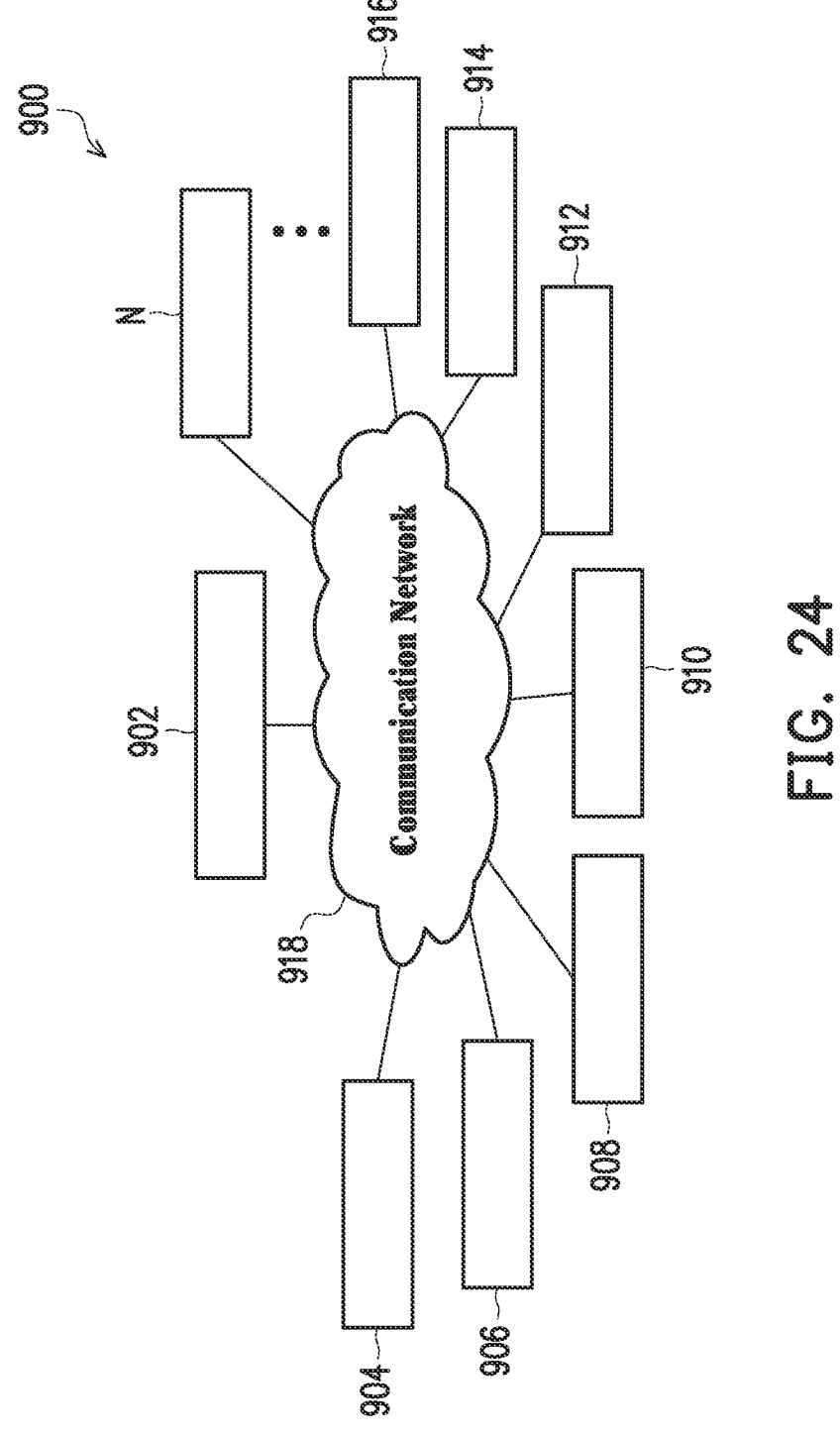
FIG. 24 is a block diagram of a manufacturing system according to various aspects of the present disclosure.

FIG. 24 illustrates an integrated circuit fabrication system 900 according to embodiments of the present disclosure. The fabrication system 900 includes a plurality of entities 902, 904, 906, 908, 910, 912, 914, 916 . . . , N that are connected by a communications network 918. The network 918 may be a single network or may be a variety of different networks, such as an intranet and the Internet, and may include both wire line and wireless communication channels.

In an embodiment, the entity 902 represents a service system for manufacturing collaboration; the entity 904 represents an user, such as product engineer monitoring the interested products; the entity 906 represents an engineer, such as a processing engineer to control process and the relevant recipes, or an equipment engineer to monitor or tune the conditions and setting of the processing tools; the entity 908 represents a metrology tool for IC testing and measurement; the entity 910 represents a semiconductor processing tool, such an EUV tool that is used to perform lithography processes to define the gate spacers of an SRAM device; the entity 912 represents a virtual metrology module associated with the processing tool 910; the entity 914 represents an advanced processing control module associated with the processing tool 910 and additionally other processing tools; and the entity 916 represents a sampling module associated with the processing tool 910.

Each entity may interact with other entities and may provide integrated circuit fabrication, processing control, and/or calculating capability to and/or receive such capabilities from the other entities. Each entity may also include one or more computer systems for performing calculations and carrying out automations. For example, the advanced processing control module of the entity 914 may include a plurality of computer hardware having software instructions encoded therein. The computer hardware may include hard drives, flash drives, CD-ROMs, RAM memory, display devices (e.g., monitors), input/output device (e.g., mouse and keyboard). The software instructions may be written in any suitable programming language and may be designed to carry out specific tasks.

The integrated circuit fabrication system 900 enables interaction among the entities for the purpose of integrated circuit (IC) manufacturing, as well as the advanced processing control of the IC manufacturing. In an embodiment, the advanced processing control includes adjusting the processing conditions, settings, and/or recipes of one processing tool applicable to the relevant wafers according to the metrology results.

In another embodiment, the metrology results are measured from a subset of processed wafers according to an optimal sampling rate determined based on the process quality and/or product quality. In yet another embodiment, the metrology results are measured from chosen fields and points of the subset of processed wafers according to an optimal sampling field/point determined based on various characteristics of the process quality and/or product quality.

One of the capabilities provided by the IC fabrication system 900 may enable collaboration and information access in such areas as design, engineering, and processing, metrology, and advanced processing control. Another capability provided by the IC fabrication system 900 may integrate systems between facilities, such as between the metrology tool and the processing tool. Such integration enables facilities to coordinate their activities. For example, integrating the metrology tool and the processing tool may enable manufacturing information to be incorporated more efficiently into the fabrication process or the APC module, and may enable wafer data from the online or in site measurement with the metrology tool integrated in the associated processing tool.

The present disclosure may offer advantages over conventional devices. However, it is understood that not all advantages are discussed herein, different embodiments may offer different advantages, and that no particular advantage is required for any embodiment. One advantage is that the improvement in sensitivity.

For example, the present disclosure implements a miniature-target sensing TFT and a voltage reference TFT on opposite sides of an opening, where the opening is configured to collect a fluid sample that contains the miniature targets. Such a unique structural design allows the miniature targets to be driven in a lateral direction, so that they are attached to one side of a sensing film disposed within the opening. This side is close to the sensing TFT, and as such, the sensing TFT is better able to detect the presence of the miniature targets. In comparison, the structural design of conventional devices may not be capable of driving the miniature targets in a manner for them to be easily attached to a portion of a sensing film that is located close to a sensing transistor, which results in a lower sensitivity or a lower signal-to-noise ratio.

Another unique feature of the present disclosure is the opening for collecting the miniature targets is wider at the top and narrower at the bottom. Such a profile allows the fluid sample containing the miniature targets to flow more easily into the opening without trapping bubbles therein. In other words, a substantial entirety of the opening may be utilized for capturing the miniature targets, which again translates into a greater signal-to-noise ratio and improves the efficiency of the miniature target detection. Furthermore, in some embodiments (see FIG. 17), the size of the drain of the sensing transistor is reduced to force more drain current to flow in a portion of the sensing transistor near the opening. Since the portion of the drain current near the opening dominates the detection of the miniature targets, the reduction of the drain of the sensing transistor also improves the sensitivity of the device.

Another advantage is the lower fabrication costs. For example, the present disclosure allows the transistors to be fabricated on a bulk semiconductor wafer, whereas conventional devices typically require a silicon-on-insulator (SOI) wafer.

Since the bulk semiconductor wafer is cheaper than the SOI wafer, the present disclosure can reduce fabrication costs. In addition, whereas conventional devices typically form the sensing and voltage reference transistors at the front end, the present disclosure forms them at the back end, for example, during the fabrication of the interconnect structure. Forming these transistors at the back end (as opposed to the front end) is also associated with a lower cost and a reduced complexity.

Other advantages may include compatibility with existing fabrication processes (including for 2-D planar devices, FinFET, and GAA processes) and the ease of implementation.

One aspect of the present disclosure pertains to a semiconductor device. The semiconductor device includes a semiconductor substrate. An interconnect structure is disposed over the semiconductor substrate. The interconnect structure includes a plurality of interconnect layers. A first thin-film transistor (TFT) and a second TFT are disposed over the semiconductor substrate. The first TFT and the second TFT each vertically extend through at least a subset of the interconnect layers. An opening is formed in the interconnect structure. The opening is disposed between the first TFT and the second TFT. A sensing film is disposed over a bottom surface and side surfaces of the opening.

Another aspect of the present disclosure pertains to a semiconductor device. The semiconductor device includes a semiconductor substrate. A first transistor and a second transistor are each formed over the semiconductor substrate. A multi-layer interconnect structure is formed over the semiconductor substrate. The first transistor and the second transistor are electrically coupled to a first interconnect layer of the multi-layer interconnect structure. The multi-layer interconnect structure includes an opening that extends partially therethrough but stops before the first interconnect layer is reached. The opening is configured to collect a fluid that contains miniature targets. Portions of a third transistor and portions of a fourth transistor each extend vertically through a subset of interconnect layers of the multi-layer interconnect structure that are located above the first interconnect layer. The third transistor and the fourth transistor are different type of transistors than the first transistor and the second transistor. The third transistors and the fourth transistors are electrically coupled to the first transistor and the second transistor, respectively. A sensing layer is formed on side surfaces and a bottom surface of the opening. The sensing layer is configured to react with or bind with the miniature targets of the fluid.

Yet another aspect of the present disclosure pertains to a method. An interconnect structure is formed over a semiconductor substrate. The interconnect structure includes a plurality of interconnect layers containing respective vias and metal lines. A first trench and a second trench are etched in the interconnect structure. A metal compound layer is deposited in the first trench and the second trench. A dielectric layer is deposited over the metal compound layer. The dielectric layer partially fills the first trench and the second trench. A conductive layer is deposited over the dielectric layer. The conductive layer completely fills the first trench and the second trench. A first thin-film transistor (TFT) is partially formed by portions of the conductive layer, the dielectric layer, and the metal compound layer filling the first trench. A second TFT is partially formed by portions of the conductive layer, the dielectric layer, and the metal compound layer filling the second trench. An opening is etched that downwardly extends at least partially through the interconnect structure. The opening is formed between the first TFT and the second TFT. A sensing film is deposited in the opening.

The foregoing outlines features of several embodiments so that those of ordinary skill in the art may better understand the aspects of the present disclosure. Those of ordinary skill in the art should appreciate that they may readily use the present disclosure as a basis for designing or modifying other processes and structures for carrying out the same purposes and/or achieving the same advantages of the embodiments introduced herein. Those of ordinary skill in the art should also realize that such equivalent constructions do not depart from the spirit and scope of the present disclosure, and that they may make various changes, substitutions, and alterations herein without departing from the spirit and scope of the present disclosure.

What is claimed is:

1. A device, comprising:
a semiconductor substrate;
an interconnect structure disposed over the semiconductor substrate, wherein the interconnect structure includes a plurality of interconnect layers;
a first thin-film transistor (TFT) and a second TFT disposed over the semiconductor substrate, wherein at least one of the first TFT and the second TFT vertically extend through at least a subset of the interconnect layers,
an opening in the interconnect structure and being configured to collect a fluid containing a miniature target, wherein the opening is disposed between the first TFT and the second TFT, and wherein a bottommost surface of the opening has a deeper depth than an uppermost surface of the first TFT; and
a sensing film disposed over a bottom surface and side surfaces of the opening, wherein the first TFT and the second TFT are configured to be electrically biased to different voltages such that the miniature target in the fluid is redistributed within the opening toward a side surface of the opening adjacent one of the first TFT or the second TFT.

2. The device of claim 1, wherein:
a side surface of the opening includes a first segment and a second segment;
the second segment is disposed closer to the semiconductor substrate than the first segment; and
a portion of the opening corresponding to the first segment is wider than a portion of the opening corresponding to the second segment.

3. The device of claim 1, wherein portions of the sensing film are disposed over a top surface of the interconnect structure.

4. The device of claim 1, wherein the sensing film includes a plurality of layers.

5. The device of claim 1, wherein at least one of the first TFT or the second TFT includes:

a metal compound layer that defines a trench that extends vertically through the subset of the interconnect layers;
a dielectric layer disposed over the metal compound layer and partially filling the trench defined by the metal compound layer; and
a conductive layer disposed over the dielectric layer and completely filling the trench defined by the metal compound layer.

6. The device of claim 5, wherein:
the metal compound layer is a part of a channel of the first or second TFT and contains Indium-Gallium-Zinc-Oxide (IGZO);
the dielectric layer is a part of a gate dielectric of the first or second TFT and contains hafnium oxide; and
the conductive layer is a part of a gate electrode of the first or second TFT and contains titanium nitride (TN).

7. The device of claim 5, further comprising:
a first non-TFT disposed between the first TFT and the semiconductor substrate, wherein the first non-TFT is electrically coupled to the first TFT through a first subset of vias and metal lines of the interconnect structure; and
a second non-TFT disposed between the second TFT and the semiconductor substrate, wherein the second non-TFT is electrically coupled to the second TFT through a second subset of vias and metal lines of the interconnect structure.

8. The device of claim 7, wherein:
the metal compound layer of the first TFT is electrically coupled to the first subset of the vias and metal lines;
the metal compound layer of the second TFT is electrically coupled to the second subset of the vias and metal lines;
the conductive layer of the first TFT is electrically coupled to a third subset of vias and metal lines of the interconnect structure; and
the conductive layer of the second TFT is electrically coupled to a fourth subset of vias and metal lines of the interconnect structure.

9. The device of claim 1, wherein:
the first TFT is a voltage-reference device;
the second TFT is a voltage-sensing device;
a channel of the first TFT is connected to a first conductive pad;
a channel of the second TFT is connected to a second conductive pad; and
the first conductive pad is wider than the second conductive pad in a cross-sectional side view.

10. The device of claim 1, wherein:
the opening is configured to collect a fluid that contains a predefined miniature target; and
the device is configured to detect a presence of the predefined miniature target.

11. The device of claim 10, wherein the miniature target includes an ion, a nucleic acid, a polarized molecule, an antigen, an antibody, an enzyme, a cell, a protein, a virus, or a bacterium.

12. A device, comprising:
a semiconductor substrate;
a first transistor and a second transistor each formed over the semiconductor substrate;
a multi-layer interconnect structure formed over the semiconductor substrate, wherein the first transistor and the second transistor are electrically coupled to a first interconnect layer of the multi-layer interconnect structure, wherein the multi-layer interconnect structure includes an opening that extends partially therethrough but stops before the first interconnect layer is reached, and wherein the opening is configured to collect a fluid that contains miniature targets;

portions of a first thin-film transistor (TFT) and portions of a second TFT each extending vertically through a subset of interconnect layers of the multi-layer interconnect structure that are located above the first interconnect layer, wherein the portion of the first TFT is electrically coupled to, and located vertically above, the first transistor, wherein the portion of the second TFT is electrically coupled to, and located vertically above, the second transistor, and wherein the opening is disposed between the first TFT and the second TFT; and a sensing layer formed on side surfaces and a bottom surface of the opening, wherein the sensing layer is configured to react with or bind with the miniature targets of the fluid, wherein the first TFT and the second TFT are configured to be electrically biased to different voltages such that the miniature targets in the fluid are redistributed within the opening toward a side surface of the opening adjacent one of the first TFT or the second TFT.

13. The device of claim 12, wherein:

the first transistor and the second transistor are non-TFTs; and the miniature targets include ions, nucleic acids, polarized molecules, antigens, antibodies, enzymes, cells, proteins, viruses, or bacteria.

14. The device of claim 12, wherein the portions of the first TFT or the portions of the second TFT further include:

a gate dielectric that forms a trench;

a gate electrode that is disposed in the trench; and a channel layer that defines the trench and that is located below the gate dielectric, wherein the channel layer contains Indium-Gallium-Zinc-Oxide (IGZO);

wherein:

the gate dielectric contains hafnium oxide; and the gate electrode contains titanium nitride.

15. The device of claim 12, wherein in a cross-sectional side view, a top portion of the opening is wider than a bottom portion of the opening.

16. A device, comprising:

a substrate;

an interconnect structure disposed over the substrate in a vertical direction in a cross-sectional side view, wherein the interconnect structure includes a plurality of interconnect layers;

an interlayer dielectric (ILD) structure disposed over the interconnect structure in the vertical direction in the cross-sectional side view;

a first transistor and a second transistor disposed over the substrate in the cross-sectional side view, wherein the first transistor and the second transistor vertically extend through a first subset of the interconnect layers, and are located below the ILD structure, in the vertical direction in the cross-sectional side view;

a recess that extends through the ILD structure and a second subset of the interconnect layers of the interconnect structure in the vertical direction in the cross-sectional side view, wherein the second subset includes a greater number of the interconnect layers than the first subset, wherein the recess is disposed between the first transistor and the second transistor in a horizontal direction in the cross-sectional side view; and a sensing film that partially fills the recess in the cross-sectional side view, wherein the first transistor and the second transistor are configured to be electrically biased to different voltages such that a miniature target in a fluid collected in the recess are redistributed within the recess toward a side surface of the recess adjacent one of the first transistor or the second transistor.

17. The device of claim 16, wherein at least one of the first transistor or the second transistor includes:

a gate dielectric as a part of a recess;

a gate electrode that is located in the recess; and a channel that contains a metal compound layer, wherein the channel defines the recess and is located below the gate dielectric.

18. The device of claim 16, further comprising:

a third transistor disposed between the first transistor and the substrate, wherein the third transistor is electrically coupled to the first transistor through a first subset of vias and metal lines of the interconnect structure; and a fourth transistor disposed between the second transistor and the substrate, wherein the fourth transistor is electrically coupled to the second transistor through a second subset of vias and metal lines of the interconnect structure.

19. The device of claim 18, wherein:

at least one of the third transistor or the fourth transistor comprises a thin-film transistor (TFT), respectively.

20. The device of claim 16, wherein:

one of the first transistor or the second transistor is a voltage-reference device;

another one of the first transistor or the second transistor is a voltage-sensing device; and the device is configured to detect a presence of the miniature target.

* * * * *